United States Patent
Afonina et al.

(10) Patent No.: US 7,205,105 B2
(45) Date of Patent: Apr. 17, 2007

(54) REAL-TIME LINEAR DETECTION PROBES: SENSITIVE 5'-MINOR GROOVE BINDER-CONTAINING PROBES FOR PCR ANALYSIS

(75) Inventors: Irina A. Afonina, Mill Creek, WA (US); Yevgeniy S. Belousov, Mill Creek, WA (US); Robert O. Dempcy, Kirkland, WA (US); Igor V. Kutyavin, Woodinville, WA (US); Sergey G. Lokhov, Kirkland, WA (US); Eugeny A. Lukhtanov, Bothell, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 306 days.

(21) Appl. No.: 10/165,410

(22) Filed: Jun. 6, 2002

(65) Prior Publication Data

US 2003/0175728 A1    Sep. 18, 2003

Related U.S. Application Data

(63) Continuation-in-part of application No. 09/876,830, filed on Jun. 6, 2001, now Pat. No. 6,790,945, which is a continuation-in-part of application No. 09/457,616, filed on Dec. 8, 1999, now Pat. No. 6,727,356.

(60) Provisional application No. 60/351,637, filed on Jan. 23, 2002, provisional application No. 60/302,137, filed on Jun. 29, 2001.

(51) Int. Cl.
C12Q 1/68 (2006.01)
C12P 19/34 (2006.01)
C07H 21/00 (2006.01)
C07H 21/02 (2006.01)
C07H 21/04 (2006.01)

(52) U.S. Cl. .......... 435/6; 435/91.1; 435/91.2; 536/23.1; 536/26.6

(58) Field of Classification Search .......... 435/6, 435/91.1, 91.2; 536/23.1, 26.6
See application file for complete search history.

(56) References Cited

U.S. PATENT DOCUMENTS

| | | |
|---|---|---|
| 4,358,535 A | 11/1982 | Palkow et al. |
| 4,458,066 A | 7/1984 | Caruthers |
| 4,683,195 A | 7/1987 | Mullis |
| 4,683,202 A | 7/1987 | Mullis |

(Continued)

FOREIGN PATENT DOCUMENTS

EP    0 320 308 B1    11/1993

(Continued)

OTHER PUBLICATIONS

Afonina et al., "Efficient priming of PCR with short oligonucleotides conjugated to a minor groove binder," Nucleic Acids Res. 25(13):2657-2660(1997).

(Continued)

*Primary Examiner*—Jezia Riley
(74) *Attorney, Agent, or Firm*—Townsend and Townsend and Crew LLP

(57) ABSTRACT

Oligonucleotide probes/conjugates are provided along with method for their use in assays to monitor amplification wherein the signal produced does not rely on 5' nuclease digestion.

8 Claims, 10 Drawing Sheets

U.S. PATENT DOCUMENTS

| | | | |
|---|---|---|---|
| 4,800,159 | A | 1/1989 | Mullis et al. |
| 4,835,263 | A | 5/1989 | Nguyen et al. |
| 4,868,103 | A | 9/1989 | Stavrianopoulos et al. |
| 4,868,105 | A | 9/1989 | Urdea et al. |
| 4,883,750 | A | 11/1989 | Whiteley et al. |
| 5,124,246 | A | 6/1992 | Urdea et al. |
| 5,210,015 | A | 5/1993 | Gelfand et al. |
| 5,237,101 | A | 8/1993 | Nicolaou et al. |
| 5,419,966 | A | 5/1995 | Reed et al. |
| 5,446,137 | A | 8/1995 | Maag et al. |
| 5,449,767 | A | 9/1995 | Ward et al. |
| 5,492,806 | A | 2/1996 | Drmanac et al. |
| 5,512,667 | A | 4/1996 | Reed et al. |
| 5,525,464 | A | 6/1996 | Drmanac et al. |
| 5,556,752 | A | 9/1996 | Lockhart et al. |
| 5,574,142 | A | 11/1996 | Meyer, Jr. et al. |
| 5,646,126 | A | 7/1997 | Cheng et al. |
| 5,659,022 | A | 8/1997 | Kutyavin et al. |
| 5,776,907 | A | 7/1998 | Kohn et al. |
| 5,786,138 | A | 7/1998 | Swenson |
| 5,801,155 | A | 9/1998 | Kutyavin et al. |
| 6,248,518 | B1 | 6/2001 | Parkhurst et al. |
| 6,312,894 | B1 * | 11/2001 | Hedgpeth et al. ............... 435/6 |
| 6,448,015 | B2 | 9/2002 | Parkhurst et al. |

FOREIGN PATENT DOCUMENTS

| | | |
|---|---|---|
| EP | 0 336 731 B1 | 5/1994 |
| EP | 0 672 677 A2 | 3/1995 |
| WO | WO 90/03370 | 4/1990 |
| WO | WO 90/14353 | 11/1990 |
| WO | WO 92/0588 | 6/1992 |
| WO | WO 92/20698 | 11/1992 |
| WO | WO 93/03736 | 3/1993 |
| WO | WO 94/17092 | 8/1994 |
| WO | WO 95/29184 | 11/1995 |
| WO | WO 96/17957 | 6/1996 |
| WO | WO 96/32496 | 10/1996 |
| WO | WO 96/40711 | 12/1996 |
| WO | WO 97/12896 | 4/1997 |
| WO | WO 98/02448 | 1/1998 |

OTHER PUBLICATIONS

Afonina et al., "Sequence-specific arrest of primer extension on single-stranded DNA by an oligonulcleotide-minor groove binder conjugate." Proc. Natl. Acad. Sci. USA, 93:3199-3204 (1996).
Agrawal et al., "Pharmacokinetics, biodistribution, and stability of oligodeoxynucleotide phosphorothioates in mice." Proc. Natl. Acad. Sci. USA, RR:7595-7599 (1991).
Animati et al., "Synthesis of two distamycin analogues and their binding mode to d(CGCAAATTTGCG)2 in the 2:1 solution complexes as determined by two dimensional H-NMR." J. Med. Chem., 38:1140-1149 (1995).
Asseline et al., "Nucleic acid-binding molecules with high affinity and base sequence specificity: Interacting agents covalently linked to oligodeoxynucleotides." Proc. Natl. Acad. Sci. USA, 81:3297-3301 (1994).
Atkinson T., and Smith M., "Solid-phase synthesis of oligodeoxyribonucleotides by the phosphite-triester method." in: *Oligonucleotide Synthesis, A Practical Approach, M.J. Gait (ed.), IRL Press Oxford*, UK, pp. 35-81 (1984).
Bailly et al., "DNA Recognition by intercalator-minor-groove binder hybrid molecules." Bioconjugate Chem. 2(6):379-393 (1991).
Bailly et al., "DNA-binding properties of a distamycin-ellipticine hybrid molecule." Mol. Pharmacol., 41:845-55 (1992).
Bailly et al., "The different binding modes of Hoechst 33258 to DNA studied by electric linear dichorism." Nucl. Acid. Res., 21(6):3705-9 (1993).
Boger et al., "CC-1065 and the duocarmycins: Unraveling the keys to a new class of naturally derived DNA alkylating agents." Proc. Natl. Acad. Sci. USA, 92:3642-3649 (1995).
Boger et al., "CC-1065 partial structures: enhancement of noncovalent affinity for DNA minor groove binding through introduction of stabilizing electrostatic interactions." J. Org. Chem., 57:1277-1284 (1992).
Boger et al., "Studies on the total synthesis of CC-1065: preparation of a synthetic, simplified 3-carbamoyl-1,2-dihydro-3H-pyrrolo[3,2-e]indole dimer/trimer/tetramer (CDPI dimer/trimer/tetramer) and development of methodology for DEP-I dimer methyl ester Formation." J. Org. Chem., 52:1521-1530 (1987).
Bolli et al., "Watson-Crick base-pairing properties of bicyclo-DNA." Nucleic Acids Res., 24:4660-4667 (1996).
Bruice et al., " Rational design of substituted tripyrrole peptides that complex with DNA by both selective minor groove binding and electrostatic interaction with the phosphate backbone." Proc. Natl., Acad. Sci. USA, 89:1700-4 (1992).
Caetano-Anolles et al., "DNA amplification fingerprinting using very short arbitrary oligonucleotide primers." Biotechnology, 9:553-557 (1991).
Cardullo et al., "Detection of nucleic acid hybridization by nonradiative fluorescence resonance energy transfer." Proc. Natl. Acad. Sci. USA, 85:8790-94 (1988).
Chen et al., "A new DNA minor groove binding motif: cross-linked lexitropsins." J. Am Chem. Soc., 116:6995-7005 (1994).
Cosstick et al., "Synthesis of d(GC) and d(CG) octamers containing alternting phosphorothioate linkages: Effect of the phosphorothioate group on the B-Z transiton." Biochemistry, 24:3630-38 (1985).
Demidov et al., "Kinetics and mechanism of polyamide ("peptide") nucleic acid binding to duplex DNA." Proc. Natl. Acad. Sci. USA, 92:2637-41 (1995).
Dempcy et al., "Synthesis of a thymidyl pentamer of deoxyribonucleic guanidine and binding studies with DNA homopolynucleotides." Proc. Natl. Acad. Sci. USA, 92:6097-101 (1995).
Dervan, "Design of sequence-specific DNA-binding molecules." Science, 232:464-71 (1986).
Don et al., "'Touchdown' PCR to circumvent spurious priming during gene amplification." Nucleic Acids Res., 19:4008 (1991).
Draper et al., "A method for linking fluorescent labels to polynucleotides: Application to studies of ribosome-ribonucleic acid interactions." Biochemistry, 19:1774-1781 (1980).
Eckstein et al., "Polyribonucleotides containing a phosphorothioate backbone." Eur. J. Biochem., 13:558-564 (1970).
Egholm, "Spectrometry senses more than a small difference." Nature Biotech., 15:1346 (1997).
Fagan et al., "Cooperative binding of distamycin-A to DNA in the 2:1 mode." J. Am Chem. Soc., 114:1080-1081 (1992)
Fodor et al., "Light-directed, spatially addressable parallel chemical synthesis." Science, 251:767-773 (1991).
Freifelder, "Fluorescence Spectroscopy." Physical Biochemistry, Second Edition, W.H. Freeman & Co., San Francisco, pp. 537-542 (1982).
Gamper et al., "Facile preparation of nuclease resistant 3' modified oligodeoxynuclcotides," Nucleic Acids Res., 21(1):145-50 (1993).
Gibson K.J. and Benkovic, S.J., "Synthesis and application of derivatizable oligonucleotides." Nucleic Acids Res., 15:6455-67 (1987).
Gibson, "A novel method for real time quantitative RT-PCR." Geonome Res., 6:995-1001 (1996).
Giovannangeli et al., "Oligonucleotide clamps arrest DNA synthesis on a single-stranded DNA target." Proc. Natl. Acad. Sci. USA, 90:10013-71 (1993).
Godovikova et al., "Reactive oligonucleotide derivatives with a Zwitter-Ionic terminal phosphate group for affinity reagents and probe construction." Bioorgan. Khim., 15:1246-1259 (1989).
Greenidge et al., "DNA minor groove recognition properties of pentamidine and its analogs: a molecular modeling study." Molecular Pharmacology. 43(6):982-988 (1993)..
Grehn L., et al., "Novel efficient total synthesis of antiviral antibiotic distamycin-A." J. Org. Chem., 46:3492-3497 (1981).

Griffin et al., "Genetic analysis by peptide nucleic acid affinity MALDI-TOF mass spectrometry." Nature Biotech., 15:1368-72 (1997).

Gryaznov et al., "Modulation of oligonucleotide duplex and triplex stability via hydrophobic interactions," Nucleic Acids Res., 21(25):5909-5915 (1993).

Gryaznov et al., "Oligodeoxyribonucleotide N3'→P5' phosphoramidates: Synthesis and hybridization properties." J. Am Chem. Soc. 116:3143-3144 (1994).

Heid et al., "Real Time Quantitative PCR." Genome Res., 6:986-994 (1996).

Holland et al., "Detection of specific polymerase chain reaction product by utilizing the 5'→3' exonuclease activity of *Thermus aquaticus* DNA polymerase." Proc. Natl. Acad. Sci. USA, 88:7276-80 (1991).

Huang et al., "Diagnosis of glucose-6-phosphate dehydrogenase (G6PD) mutations by DNA amplification and allele-specific oligonucleotide probes." Acta Haematol., 88:92-95 (1992).

Hurley and Boyd, "Approaches toward the design of sequence-specific drugs for DNA." Ann. Rep. Med. Chem., 22(26):259-68 (1987).

Hurley et al., "Reaction of the antitumor antibiotic CC-1065 with DNA: Structure of a DNAadduct with DNA sequence specificity." Science, 226(4676):843-844 (1984).

Inoue et al., "Synthesis and hybridization studies on two complementary nona(2'-O-methyl)ribonucleotides." Nucleic Acids Res., 15(15):6131-6148 (1987).

Jones, "Preparation of protected deoxyribonucleotides." in: *Oligonucleotide Synthesis, A Practical Approach* M.J. Gait (ed.), IRL Press, Oxford, UK, pp. 23-34 (1984).

Jost et al., "Quantitative precipitation of short oligonucleotides with low concentrations of cetyltrimethylammonium bromide." Nucleic Acids Res., 17(5):2143 (1989), Kazimierczuk et al., "Synthesis of 2'-deoxytubercidin, 2'-deoxyadenosine, and related 2-deoxynucleosides via a novel direct stereospecific sodium salt glycosylation procedure." J. Am Chem. Soc., 106:6379-6382 (1984).

Kenten et al., "Rapid electrochemiluminescence assays of polymerase chain reaction products." Clin. Chem., 37(9):1626-32 (1991).

Kessler (ed.), *Nonradioactive labeling and Detection of Biomolecules*, Springer-Verlag, Berlin, pp. 13-14 (1992).

Kim et al., "Helix-stabilizing agent, CC-1065, enhances suppression of translation by an antisense oligodeoxynucleotide." Antisense Res. Dev., 5:149-154 (1995).

Kim et al., "Helix-stabilizing compounds CC-1065 and U-71, 184 bind to RNA-DNA and DNA-DNA duplexes containing modified internucleotide linkages and stabilize duplexes against thermal melting." Antisense Res. Dev., 5:49-57 (1995).

Kopka et al., "Bindig of an antitumor drug to DNA netropsin and C-G-C-G-A-A-T-T-C-G-C-G." J. Mol. Biol., 183:553-63 (1985).

Kubista et al., "Characterization of interaction between DNA and 4-40 ,6-diamidino-2-phenylindole by optical spectroscopy." Biochemistry, 26:4545-4553 (1987).

Lamm et al., "Antisense probes containing 2-aminoadenosine allow efficient depletion of U5 snRNP from HeLa splicing extracts." Nucleic Acids Res., 19(12):3193-3198 (1991).

Lander, "The new genomics: Global views of biology." Science, 274:536-39 (1996).

LaPlanche et al., "Phosphorothioate-modified oligodeoxyribonucleotides. III. NMR and UV spectroscopic studies of the $R_p$-$R_p$, $S_p$-$S_p$, and $R_p$-$S_p$ duplexes, d(GG$_s$AATCC)$_2$, derived from diasteromeric O-ethyl phosphorothioates." Nucleic Acids Res., 14(22):9081-9093 (1986).

Larhammar et al., " Exon-intron organization and complete nucleotide sequence of a human major histocompatibility antigen DCβ gene." Proc. Natl. Acad. Sci. USA, 80:7313-7317 (1983).

Lee et al., "Allelic discrimination by nick-translation PCT with fluorogenic probes." Nucleic Acids Res., 21(16):3761-66 (1993).

Lee et al., "Mapping of DNA alkylation sites induced by adozelesin and bizelesin in human cells by ligation-mediated polymerase chain reaction." Biochemistry 33:6024-6030 (1994).

Liang et al., " Differential display of eukaryotic messenger RNA by means of the Polymerase chain reaction." Science, 257:967-971 (1992).

Little et al., "Mass spectrometry from miniaturized arrays for full comparative DNA analysis." Nature Med., 3(12):1413-16 (1997).

Livak et al., Oligonucleotides with fluorescent dyes at opposit ends provide a quenched probe system useful for detecting pcr product and nucleic hybridization, PCR Meth. and App., 4:357-362 (1995).

Lokhov et al., "Synthesis and high stability of complementary complexes of N-(2-hydroxyethyl)phenazinium derivatives of oligonucleotides." Bioconjugate Chem., 3:414-419 (1992).

Lukhtanov et al., "Direct, solid phase assembly of dihydropyrroloindole peptides with conjugated oligonucleotides." Bioconjugate Chem., 7:564-567 (1996).

Lukhtanov et al., "Oligodeoxyribonucleotides with conjugated dihydropyrroloindole oligopeptides: preparation and hybridization properties." Bioconjugate Chem., 6:418-426 (1995).

Lutz et al., "Recognition of uncharged polyamide-linked nucleic acid analogs by DNA polymerases and reverse transcriptases." J. Am. Chem. Soc., 119:3177-78 (1997).

Marck et al., "Specific interaction of netropsin, distamycin-3 and analogs with I.C duplexes: reversion towards the B form of the 2'deoxy-.2'deoxy-2'-fluoro-hybrid duplexes upon specific interaction with netropsin, distamycin-3 and analogs." Nucleic Acids Res., 10(19):6147-6161 (1982).

Marky and Breslauer, "Origins of netropsin binding affinity and specificity: Correlations of thermodynamic and structural data." Proc. Natl. Acad. Sci. USA, 84:4359-63 (1987).

Marsch et al., "Non-covalent DNA groove-binding by 2-amino-1-methyl-6-phenylimidazo[4,5-b]pyridine." Nucl. Acid Res., 22(24):5408-15 (1994).

Marshall, "'Playing chicken' over gene markers." Science, 278:2046-48 (1997).

Marshall, "Snipping away at genome patenting." Science, 277:1752-53 (1997).

Mohan et al., "Flexibility of DNA in 2:1 drug-DNA complexes-simultaneous binding of two DAPI molecules to DNA." J. Biomol. Struct. Dyn., 9(3):695-704 (1994).

Monia et al., "Evaluation of 2'-modified oligonucleotides containing 2'-deoxy gaps as antisense inhibitors of gene expression." J. Biol. Chem., 268(19):14514-14522 (1993).

Moon et al., "DNA structural features responsible for sequence-dependent binding eometries of Hoescht 33258." Biopolymers, 38:593-606 (1996).

Moran et al., "A thymidine triphosphate shape analog lacking Watson-Crick pairing ability is replicated by high sequence selectivity." Proc. Natl. Acad. Sci. USA, 94:10506-511 (1997).

Mrksich et al., "Antiparallel side-by-side dimeric motif for sequence-specific recognition in the minor groove of DNA by the designed peptide 1-methylimidazole-2-carboxamide netropsin." Proc. Natl. Acad. Sci. USA, 89:7586-7590 (1992).

Mullis and Faloona, "Specific synthesis of DNA *in vitro* via a polymerase-catalyzed chain reaction." Meth. Enzymol., vol. 155:335-50, Academic Press, New york (1987).

Nielsen et al., "Peptide nucleic acid (PNA) A DNA mimic with a peptide backbone." Bioconjugate Chem., 5:3-7 (1994).

Nielsen et al., "Sequence-selective recognition of DNA by strand displacement with a thymine-substituted polyamide." Science, 254:1497-1500 (1991).

Ørum et al. "Single base pair mutation analysis by PNA directed PCR clamping." Nucleic Acid Research, 21(23):5332-5336 (1993).

Parris et al., "A signature clement distinguishes sibling and independent mutations in a shuttle vector plasmid." Gene, 117:1-5 (1992).

Pastinen et al., "Minisequencing: A specific tool for DNA analysis and diagnostics on obligonucleotid arrays." Genome Res., 7:606-14 (1997).

Patel, "Antibiotic-DNA interactions: Intermolecular nuclear Overhauser effects in the netropsin-d(C-G-C-G-A-A-T-T-C-G-C-G) complex.in solution." Proc. Natl. Acad. Sci. USA, 79:6424-28 (1982).

Petrie et al., "An improved CPG support for the synthesis of 3'-amine- tailed oligonucleotides." Bioconjugate Chemistry, 3:8—n (1992).

Rao et al., "Synthesis of novel thiazole-containing DNA minor groove binding oligopeptides related to the antibiotic distamycin." 1. Org. Chem., 55:728-737 (1990).

Reed el al "Acridine- and cholesterol-derivatized solid supports for improved synthesis of 3'-modified oligonucleotides." Bioconjugate Chem., 2:217-225 (1991).

Remers et al., "Conformations of complexes between pyrrolo[1,4]benzodiazepines and DNA segments." J. Med. Chem, 29:2492-503 (1986).

Reynolds et al., "Reaction of the antitumor antibiotic cc-1065 with DNA. Location of the site of thermally induced strand breakage and analysis of dna sequence specificity." Biochemistry, 24:6228-6237 (1985).

Risch, "The future of genetic studies of complex human diseases." Science, 273:1516-17 (1996).

Robins et al., "Nucleic acid related compounds. 38. Smooth and high-yield iodination and chlorination at C-5 or uracil bases and p-toluyl-protected nucleosides." Can. .T. Chem., 60:554-557 (1982).

Robins et al., "Nucleic acid related compounds. 39. Efficient conversion of 5-iodo to 5-alkynyl and derived 5-substituted uracil base and nucleosides." J. Org. Chem., 48:1854-1862 (1983).

Rougeon et al., "Insertion of a rabbit β-globin gene sequence into an E. coli plasmid." Nucleic Acids Res, 2(12):2365-2378 (1975).

Saiki et al., "Enzymatic amplification of β-globin genomic sequences and restriction site analysis for diagnosis of sickle cell anemia." Science, 230:1350-1354 (1985).

Saiki, "The Design and Optimization of the PCR." in: PCR Technology: Principles and Applications for DNA Amplification. Erlich, H.A. (ed.), Chapter 1, pp. 7-16, Stockton Press, (1989).

Sanger et al., "DNA sequencing with chain-terminating inhibitors." Proc. Natl. Acad. Sci. USA., 74:5463-5467 (1977).

Scahill et al., "An NMR study of the covalent and noncovalent interactions of CC-1065 and DNA." Biochemistry, 29:2852-2860 (1990).

Schaffer et al., "DNA variation and the future of human genetics." Nature Biotechnology, 16:33-39 (1998).

Seela and Driller, "Alternating $d(G-C)_3$ and $d(C-G)_3$ hexenucleotides containing 7-deaza-2'-deoxyguanosine or 8-aza-7-deaza-2'-deoxyguanosine in place of dG." Nucl. Acid Res., 17(3):901-10 (1989).

Seela and Mehkhoff, "2'-deoxiribofuranosides of 6-oxoallopurinol and of related 4,6-disubstituted pyrazolo[3,4-d] pyrimidines" Liebigs Ann. Chem. 1986, 1213-21 (1986) (in German, with English Abstract).

Seela and Steker, "Synthesis of 2'-deoxyribofuranosides of 8-aza-7-deazaguanine and related pyrazolo[3,4-d]pyrimidines" Helv. Chim. Acta. 69(7):1602-1613 (1986).

Shabarova et al., "DNA-like duplexes with repetitions. III. Efficient template-guided chemical polymerization of d(TGGCCAAGCTp)." Nucleic Acids Res., 9:5747-5761 (1981).

Shuber et al., "High throughput parallel analysis of hundreds of patient samples for more than 100 mutations in multiple disease genes." Hum. Mol. Genet., 6(3):337-47 (1997).

Singh et al., "Isoelicity and strand selectivity in the minor groove binding of chiral (1R,2R)- and (1S,2S)-bis(netropsin)-1,2-cyclopropanedicarboxamide ligands to duplex DNA." J. Am. Chem. Soc., 116:7006-20 (1994).

Singh et al., "Synthesis and sequence-specific DNA binding of a topoisomerase inhibitory analog of Hoechst 33258 designed for altered base and sequence recognition." Chem. Res. Toxocol., 5:597-607 (1992).

Sinyakov et aL, "Exceptional and selective stabilization of A-T rich DNA-DNA duplexes by N-methylpyrrole carboxamide peptides conjugated to oligodeoxynucleotides." J. Am Chem. Soc., 117:4995-4996 (1995).

Smits et al., "Detection and typing of human papillomaviruses present in fixed and stained archival cervical smears by a consensus polymerase chain reaction and direct sequence analysis allow the identification of a broad spectrum of human papillomavirus types." J. Gen Virol., 73:3263-3268 (1992).

Sonveaux, "The organic chemistry underlying DNA synthesis." Bioinorgan. Chem., 14:274-325 (1986).

Spielman et al., "Transmission test for linkage disequilibrium: The insulin gene region and insulin-dependent diabetes mellitus (IDDM)." Am. J. Hum. Genet. 52:506-16 (1993).

Sproat et al., "2'-O-alkyloligoribonucleotides." in: Antisense Research and Applications, Crooke, ST. and Lebleu, B. (eds), pp. 351-362, CRC Press, Boca Raton, Fla. (1993).

Stein et al., "Physiochemical properties of phosphorothioate oligodeoxynucleotides." Nucleic Acids Res., 16(8):3209-3221 (1988).

Suggs et al., "Evidence for sequence-specific conformational changes in DNA from the melting temperatures of DNA phosphorothioate derivates." Nucleic Acids Res., 13(15):5707-5716 (1985).

Tabone et al., "Factors influencing the extent and regiospecificity of cross-link fonnation between single stranded DNA and reactive complementary oligodeoxynucleotides." Biochemistry, 33:375-383 (1994).

Tautz, "Notes on the definition and nomenclature of tandemly repetitive DNA sequences." in: DNA Fingerprinting: State of the Science, Pena et al. (ed.), pp. 21-28, Birkauser, Basel, (1993).

Trotta et al., "$^1$H NMR study of $[d(GCGATCGC)]_2$ and its interaction with minor groove binding 4',6-diaminido-2-phenylindole." J. Biol. Chem., 268(6):3944-51 (1993).

Tung et al., "PCR Amplification of Specific Sequences from a cDNALibrary." in: PCR Tehnology: Principles and Applications for DNA Amplification, Erlich, H.A. (ed.), Chapter 9, pp. 99-104, Stockton Press(1989).

Turner et al., "The mutagenic properties of DNA minor-groove binding ligands." Mutation Research. 355:141-169 (1996).

Uhlmann et al., "Synthesis and properties of PNA/DNA chimeras." Angew. Chem. Int. Ed., Engl., 35(22):2632-35 (1996).

Uhlmann et al., "Synthesis of polyamide nucleic acids (PNAs), PNA/DNA-chimeras and phosphonic ester nucleic acids (PHONAs)." Nucleosides & Nucleotides, 16(5&6):603-8 (1997).

van der Laan et al., "A convenient automated solid-phase synthesis of PNA-(5')-DNA-(3')-PNA chimera. " Tetrahedron Lett., 38(13): 2249-52 (1997).

van der Laan et al., "Solid support synthesis of a PNA-DNA hybrid." Recl. Trav. Chim. Pays-Bas, 114:295-7 (1995).

van Ness et al., "The use of oligodeoxynucleotide probes in chaotrope-based hybridization solutions." Nucleic Acids Res., 19:5143-5151 (1991).

Wagner et al., "Antisense gene inhibition by oligonucleotides containing C-5 propyne pyrimidines." Science, 260:1510-1513 (1993).

Wartell et al., "Netropsin: A specific probe for A-T regions of duplex deoxyribonucleic acid." J. Biol. Chem., 249(21):6719-6731 (1974).

Webb et al., "Hybridization triggered cross-linkage of deoxyoligonucleotides." Nucleic Acids Res., 14:7661-7674 (1986a).

Webb et al.; "Sequence-Specific Cross-Linking of Deoxyoligonucleotides via Hybridization-Triggered Alkylation." J. Am Chem. Soc., 108:2764-2765 (1986b).

Wemmer et al., "Targeting the minor groove of DNA." Curr. Opin. Struct. Biol. 7(3):355-361 (1997).

Wiederholt et al., "DNA-tethered Hoechst groove-binding agents: Duplex stabilization and fluorescence characteristics." J. Am Chem. Soc., 118:7055-7062 (1996).

Wiederholt et al., "Oligonucleotides tethering Hoechst 33258 derivatives: Effect of the conjugation site on duplex stabilization and fluorescence properties." Bioconjugate Chem., 8:119-126 (1997).

Williams et al., "Genetic analysis using random amplified polymorphic DNA markers." in Methods in Enzymology, 218(1):704-740, Academic Press, New York (1993).

Wittwer et al., "Continuous fluorescence monitoring of rapid cycle DNA amplification." Biotechniques, 22(1):130-138 (1997).

Wittwer et al., "The LightCycler™ : A microvolume multisample fluorimeter with rapid temperature control." *Biotechniques*, 22(1):176-181 (1997).

Afonina et al., "accurate snp typing by real-time pcr. a comparison of minor groove binder-conjugated dna probes", *Pharmagenomics*, Jan./Feb. 2002, pp. 48-54 (XP002345315).

Kutyavin I. V. et al., "3-minor groove binder-DNA probes increase sequence specificity at pcr extension temperatures", *Nucleic Acids Research*, Oxford University Press, Surrey, GB, vol. 28, No. 2, 2000, pp.655-661 (XP002318952).

Afonina et al., "efficient priming of pcr with short oligonucleotides conjugated to a minor groove binder", *Nucleic Acids Research*, Oxford University Press, Surrey, GB, vol. 25, No. 13, 1997, pp. 2657-2660 (XP002111427).

Afonina 1. et al., "sequence-specific arrest of primer extension on single-stranded dnab an olgonucleotide-minor groove binder conjugate", *Proceedings of the National Academy of Sciences of USA, National Academy of Science*. Washington, US, vol. 93, Apr. 1996, pp. 3199-3204 (XP000574996).

* cited by examiner

$T_m$ Dissociation Curves of MTHFR Alleles – Post Eclipse™ Amplification

Wild Type
MGB-Q-ATC GGC TCC CGC-FAM

Mutant
MGB-Q-AAT CGA CTC CCG C-YY

SEQUENCE LISTING

```
<160> NUMBER OF SEQ ID NOS: 43

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence:5'-minor
      groove binder-quencher-oligonucleotide-fluorophore
      (5'-MGB-Q-ODN-Fl) conjugate
<220> FEATURE:
<221> NAME/KEY: modified_base
<222> LOCATION: (1)
<223> OTHER INFORMATION: n = c modified by quencher (Q) and minor groove
      binder (MGB)
<220> FEATURE:
<221> NAME/KEY: modified_base
<222> LOCATION: (13)
<223> OTHER INFORMATION: n = c modified by fluorophore (Fl)

<400> SEQUENCE: 1
nattttagtc ctn                                                        13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence:CYP2D6
      allele "C" probe, Eclipse probe allele 1 (WT)
<220> FEATURE:
<221> NAME/KEY: modified_base
<222> LOCATION: (1)
<223> OTHER INFORMATION: n = c modified by quencher (Q) and minor groove
      binder (MGB)
<220> FEATURE:
<221> NAME/KEY: modified_base
<222> LOCATION: (8)..(10)
<223> OTHER INFORMATION: n = guanine analogue
      6-amino-1H-pyrazolo[3,4-d]pyrimidin-4(5H)-one
      (PPG or Super G)
<220> FEATURE:
<221> NAME/KEY: modified_base
<222> LOCATION: (13)
<223> OTHER INFORMATION: n = g modified by 6-carboxyfluorescein (FAM)

<400> SEQUENCE: 2
ngtcctgngn gtn                                                        13
```

```
<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence:CYP2D6*4
      allele "T" probe, Eclipse probe allele 1 (mutant)
<220> FEATURE:
<221> NAME/KEY: modified_base
<222> LOCATION: (1)
<223> OTHER INFORMATION: n = g modified by quencher (Q) and minor groove
      binder (MGB)
<220> FEATURE:
<221> NAME/KEY: modified_base
<222> LOCATION: (10)..(12)
<223> OTHER INFORMATION: n = guanine analogue
      6-amino-1H-pyrazolo[3,4-d]pyrimidin-4(5H)-one
      (PPG or Super G)
<220> FEATURE:
<221> NAME/KEY: modified_base
<222> LOCATION: (14)
<223> OTHER INFORMATION: n = t modified by "Yakima Yellow" (YY)

<400> SEQUENCE: 3
ngcgtcttgn gngn                                                       14

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence:wild-type
      MTHFR allele probe
<220> FEATURE:
<221> NAME/KEY: modified_base
<222> LOCATION: (1)
<223> OTHER INFORMATION: n = a modified by quencher (Q) and minor groove
      binder (MGB)
<220> FEATURE:
<221> NAME/KEY: modified_base
<222> LOCATION: (12)
<223> OTHER INFORMATION: n = c modified by 6-carboxyfluorescein (FAM)

<400> SEQUENCE: 4
ntcggctccc gn                                                         12

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence:mutant MTHFR
      allele probe
<220> FEATURE:
<221> NAME/KEY: modified_base
<222> LOCATION: (1)
<223> OTHER INFORMATION: n = a modified by quencher (Q) and minor groove
      binder (MGB)
<220> FEATURE:
<221> NAME/KEY: modified_base
<222> LOCATION: (13)
<223> OTHER INFORMATION: n = c modified by "Yakima Yellow" (YY)

<400> SEQUENCE: 5
natcgactcc cgn                                                        13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence:preferred
```

```
      MGB-Eclipse probe (5'-MGB-Q-ODN-Fl)
<220> FEATURE:
<221> NAME/KEY: modified_base
<222> LOCATION: (1)
<223> OTHER INFORMATION: n = c modified by quencher (Q) and minor groove
      binder (MGB)
<220> FEATURE:
<221> NAME/KEY: modified_base
<222> LOCATION: (13)
<223> OTHER INFORMATION: n = c modified by fluorophore (Fl)

<400> SEQUENCE: 6
nattttagtg ctn                                                          13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence:related MGB
      TaqMan probe (3'MGB-Q-ODN-Fl)
<220> FEATURE:
<221> NAME/KEY: modified_base
<222> LOCATION: (1)
<223> OTHER INFORMATION: n = c modified by fluorophore (Fl)
<220> FEATURE:
<221> NAME/KEY: modified_base
<222> LOCATION: (13)
<223> OTHER INFORMATION: n = c modified by quencher (Q) and minor groove
      binder (MGB)

<400> SEQUENCE: 7
nattttagtg ctn                                                          13

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:RRM1 T1037G
      mutation Primer 1 (sense)

<400> SEQUENCE: 8
atggccttgt accgatgctg a                                                 21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: RRM1 T1037G
      mutation Primer 2 (antisense)

<400> SEQUENCE: 9
gtactttcaa ttcatggagc atacct                                            26

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:RRM1 T1037G
      mutation MGB Eclipse probe allele 1 (sense)
<220> FEATURE:
<221> NAME/KEY: modified_base
<222> LOCATION: (1)
<223> OTHER INFORMATION: n = a modified by quencher (Q) and minor groove
      binder (MGB)
<220> FEATURE:
<221> NAME/KEY: modified_base
<222> LOCATION: (17)
```

<223> OTHER INFORMATION: n = a modified by 6-carboxyfluorescein (FAM)

<400> SEQUENCE: 10
ntatctagct gtgttgn                                                  17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:RRM1 T1037G
      mutation MGB Eclipse probe allele 2  (sense)
<220> FEATURE:
<221> NAME/KEY: modified_base
<222> LOCATION: (1)
<223> OTHER INFORMATION: n = a modified by quencher (Q) and minor groove
      binder (MGB)
<220> FEATURE:
<221> NAME/KEY: modified_base
<222> LOCATION: (17)
<223> OTHER INFORMATION: n = a modified by
      6-carboxy-4,7,2',7'-tetrachlorofluorescein (TET)

<400> SEQUENCE: 11
ntatcgagct gtgttgn                                                  17

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:RRM1 T1037G
      mutation MGB-TaqMan allele 1 (sense)
<220> FEATURE:
<221> NAME/KEY: modified_base
<222> LOCATION: (1)
<223> OTHER INFORMATION: n = a modified by 6-carboxyfluorescein (FAM)
<220> FEATURE:
<221> NAME/KEY: modified_base
<222> LOCATION: (16)
<223> OTHER INFORMATION: n = g modified by quencher (Q) and minor groove
      binder (MGB)

<400> SEQUENCE: 12
ntatctagct gtgttn                                                   16

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:CYP2D6*4
      Primer 1 (sense)

<400> SEQUENCE: 13
tgatgggcag aagggcacaa                                               20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:CYP2D6*4
      Primer 2 (antisense)

<400> SEQUENCE: 14
atcacgttgc tcacggcttt gtc                                           23

<210> SEQ ID NO 15

```
<211> LENGTH: 20
<212> TYPE: DNA
<213> ORGANISM: Artificial Sequence
<220> FEATURE:
<223> OTHER INFORMATION: Description of Artificial Sequence:human herpes
      virus 1,2 Primer 1 (sense)

<400> SEQUENCE: 15
atccgaacgc agccccgctg                                                 20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:human herpes
      virus 1,2 Primer 2 (antisense)

<400> SEQUENCE: 16
tctccgtcca gtcgtttatc ttc                                             23

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:human herpes
      virus 1,2 Eclipse probe (antisense)
<220> FEATURE:
<221> NAME/KEY: modified_base
<222> LOCATION: (1)
<223> OTHER INFORMATION: n = c modified by quencher (Q) and minor groove
      binder (MGB)
<220> FEATURE:
<221> NAME/KEY: modified_base
<222> LOCATION: (17)
<223> OTHER INFORMATION: n = t modified by 6-carboxyfluorescein (FAM)

<400> SEQUENCE: 17
nccaggttat cctcgcn                                                    17

<210> SEQ ID NO 18
<211> LENGTH: 900
<212> TYPE: DNA
<213> ORGANISM: Homo sapiens
<220> FEATURE:
<223> OTHER INFORMATION: portion of cytochrome P450 2D6 gene (CYP2D6*4
      allele)

<400> SEQUENCE: 18
gggtcttccc tgagtgcaaa ggcggtcagg gtgggcagag acgaggtggg gcaaagcctg    60
ccccagccaa gggagcaagg tggatgcaca aagagtgggc cctgtgacca gctggacaga   120
gccagggact gcgggagacc aggggagca tagggttgga gtgggtggtg gatggtgggg    180
ctaatgcctt catggccacg cgcacgtgcc cgtcccaccc ccaggggtgt tcctggcgcg   240
ctatgggccc gcgtggcgcg agcagaggcg cttctccgtg tccaccttgc gcaacttggg   300
cctgggcaag aagtcgctgg agcagtgggt gaccgaggag gccgcctgcc tttgtgccgc   360
cttcgccaac cactccggtg ggtgatgggc agaagggcac aaagcgggaa ctgggaaggc   420
gggggacggg gaaggcgacc ccttacccgc atctcccacc ccargacgc ccctttcgcc    480 ccaacggtct cttggacaaa gccgtgagca acgtgatcgc ctccctcacc tgcgggcgcc   540
gcttcgagta cgacgaccct cgcttcctca ggctgctgga cctagctcag gagggactga   600
aggaggagtc gggctttctg cgcgaggtgc ggagcgagag accgaggagt ctctgcaggg   660
```

```
cgagctcccg agaggtgccg gggctggact ggggcctcgg aagagcagga tttgcataga    720
tgggtttggg aaaggacatt ccaggagacc ccactgtaag aagggcctgg aggaggaggg    780
gacatctcag acatggtcgt gggagaggtg tgcccgggtc aggggcacc aggagaggcc     840 aaggactctg tacctcctat ccacgtcaga gatttcgatt ttaggtttct cctctgggca    900
```

<210> SEQ ID NO 19
<211> LENGTH: 13
<212> TYPE: DNA
<213> ORGANISM: Artificial Sequence
<220> FEATURE:
<223> OTHER INFORMATION: Description of Artificial Sequence:CYP2D6*4 WT
      probe
<220> FEATURE:
<221> NAME/KEY: modified_base
<222> LOCATION: (8)..(10)
<223> OTHER INFORMATION: n = guanine analogue
      6-amino-1H-pyrazolo[3,4-d]pyrimidin-4(5H)-one
      (PPG or Super G)

<400> SEQUENCE: 19
cgtcctgngn gtg                                                       13

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence:CYP2D6*4
      mutant probe
<220> FEATURE:
<221> NAME/KEY: modified_base
<222> LOCATION: (10)..(12)
<223> OTHER INFORMATION: n = guanine analogue
      6-amino-1H-pyrazolo[3,4-d]pyrimidin-4(5H)-one
      (PPG or Super G)

<400> SEQUENCE: 20
ggcgtgttgn gngt                                                      14

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence:CYP2D6*4 WT
      probe
<220> FEATURE:
<221> NAME/KEY: modified_base
<222> LOCATION: (9)..(11)
<223> OTHER INFORMATION: n = guanine analogue
      6-amino-1H-pyrazolo[3,4-d]pyrimidin-4(5H)-one
      (PPG or Super G)

<400> SEQUENCE: 21
cgtcctggng ntg                                                       13

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:CYP2D6*4
      Primer 2

<400> SEQUENCE: 22
tcacgttgct cacggctttg tc                                             22

```
<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:CYP2D6*4
      Primer 2

<400> SEQUENCE: 23
tgatgggcag aagggcacaa a                                              21

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence:beta-actin
      gene Primer 1 sense

<400> SEQUENCE: 24
gcgtgatggt gggcat                                                    16

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:beta-actin
      gene Primer 2 antisense
<220> FEATURE:
<221> NAME/KEY: modified_base
<222> LOCATION: (5)
<223> OTHER INFORMATION: n = guanine analogue
      6-amino-1H-pyrazolo[3,4-d]pyrimidin-4(5H)-one
      (PPG or Super G)

<400> SEQUENCE: 25
gatgnggtac ttcagggt                                                  18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:beta-actin
      gene detection probe sense
<220> FEATURE:
<221> NAME/KEY: modified_base
<222> LOCATION: (1)
<223> OTHER INFORMATION: n = g modified by quencher (Q) and minor groove
      binder (MGB)
<220> FEATURE:
<221> NAME/KEY: modified_base
<222> LOCATION: (18)
<223> OTHER INFORMATION: n = a modified by 6-carboxyfluorescein (FAM)

<400> SEQUENCE: 26
ngattcctat gtgggcgn                                                  18

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence:RRM1 T1037
      mutation Molecular beacon allele 1 (sense)
<220> FEATURE:
<221> NAME/KEY: modified_base
<222> LOCATION: (1)
<223> OTHER INFORMATION: n = c modified by 6-carboxyfluorescein (FAM)
<220> FEATURE:
```

```
<221> NAME/KEY: modified_base
<222> LOCATION: (34)
<223> OTHER INFORMATION: n = g modified by dabcyl

<400> SEQUENCE: 27
ncaaccatcc acatatctag ctgtgttggg ttgn                         34

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence:background
      fluorescence probe sequence

<400> SEQUENCE: 28
tcctgatttt ac                                                 12

<210> SEQ ID NO 29
<211> LENGTH: 351
<212> TYPE: DNA
<213> ORGANISM: Artificial Sequence
<220> FEATURE:
<223> OTHER INFORMATION: Description of Artificial Sequence:AT-rich
      region

<400> SEQUENCE: 29
ttaacaaaag tattagtaat catattactt tcttaatct gtgtggtgag tacgtaagtg      60
ttcatttcca ttccattagt attatatttg aaaactaaaa actcctgcgt aagtctcaat   120
ataactgctt atgtccatgt tctatttaat acaccttata acccatgtgt agtgtgaacc   180
aatagctgtg ttttaatatt tttgytaaat atattataca ttcactataa cctctacagt   240
tttaaagaat gttaaaatga acctgaatac ctagtttcct ctacccacac ccttctcccc   300
cataccaatc tttacttcac aattctgtca attacagctt aggaaggtac t            351

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:Sense Primer
      1
<220> FEATURE:
<221> NAME/KEY: modified_base
<222> LOCATION: (3)..(13)
<223> OTHER INFORMATION: n =
      5-(4-hydroxy-but-1-ynyl)-1H-pyrimidine-2,4-dione
      (Super T)
<220> FEATURE:
<221> NAME/KEY: modified_base
<222> LOCATION: (15)
<223> OTHER INFORMATION: n =
      4,(4,6-diamino-1H-pyrazolo[3,4-d]pyrimidin-3-yl)-
      but-3-yn-1-ol (Super A)

<400> SEQUENCE: 30
ccngcgnang ncncnatat                                          19

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence:Antisense
      Primer 2
<220> FEATURE:
<221> NAME/KEY: modified_base
```

```
<222> LOCATION: (2)..(4)
<223> OTHER INFORMATION: n =
      5-(4-hydroxy-but-1-ynyl)-1H-pyrimidine-2,4-dione
      (Super T)
<220> FEATURE:
<221> NAME/KEY: modified_base
<222> LOCATION: (7)
<223> OTHER INFORMATION: n =
      4,(4,6-diamino-1H-pyrazolo[3,4-d]pyrimidin-3-yl)-
      but-3-yn-1-ol (Super A)

<400> SEQUENCE: 31
cngnagnggt tatagtg                                                  17

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence:Probe "T"
<220> FEATURE:
<221> NAME/KEY: modified_base
<222> LOCATION: (1)
<223> OTHER INFORMATION: n = t modified by quencher (Q) and minor groove
      binder (MGB)
<220> FEATURE:
<221> NAME/KEY: modified_base
<222> LOCATION: (2)..(4)
<223> OTHER INFORMATION: n =
      5-(4-hydroxy-but-1-ynyl)-1H-pyrimidine-2,4-dione
      (Super T)
<220> FEATURE:
<221> NAME/KEY: modified_base
<222> LOCATION: (6)..(15)
<223> OTHER INFORMATION: n =
      4,(4,6-diamino-1H-pyrazolo[3,4-d]pyrimidin-3-yl)-
      but-3-yn-1-ol (Super A)
<220> FEATURE:
<221> NAME/KEY: modified_base
<222> LOCATION: (16)
<223> OTHER INFORMATION: n =
      5-(4-hydroxy-but-1-ynyl)-1H-pyrimidine-2,4-dione
      (Super T) modified by
      6-carboxy-4,7,2',7'-tetrachlorofluorescein (TET)

<400> SEQUENCE: 32
nngntnantn tnttnn                                                   16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence:Probe "C"
<220> FEATURE:
<221> NAME/KEY: modified_base
<222> LOCATION: (1)
<223> OTHER INFORMATION: n =
      5-(4-hydroxy-but-1-ynyl)-1H-pyrimidine-2,4-dione
      (Super T) modified by quencher (Q) and minor
      groove binder (MGB)
<220> FEATURE:
<221> NAME/KEY: modified_base
<222> LOCATION: (2)..(15)
<223> OTHER INFORMATION: n =
      4,(4,6-diamino-1H-pyrazolo[3,4-d]pyrimidin-3-yl)-
      but-3-yn-1-ol (Super A)
<220> FEATURE:
<221> NAME/KEY: modified_base
<222> LOCATION: (16)
<223> OTHER INFORMATION: n = t modified by 6-carboxyfluorescein (FAM)

<400> SEQUENCE: 33
nngctnantn tnttnn                                                   16
```

```
<210> SEQ ID NO 34
<211> LENGTH: 71
<212> TYPE: DNA
<213> ORGANISM: Artificial Sequence
<220> FEATURE:
<223> OTHER INFORMATION: Description of Artificial Sequence:Universal
      Internal Control (IC) (scrambled C. elegans
      sequence)

<400> SEQUENCE: 34
ctcaggtgtc cgtgtgttcc atctgttcta ggcaaagtcc catcgtttcc accagttact        60
ttacggacca c                                                             71

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence:Forward
      Universal Internal Control (IC) primer

<400> SEQUENCE: 35
ctcaggtgtc cgtgtgttcc at                                                 22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:Reverse
      Universal Internal Control (IC) primer

<400> SEQUENCE: 36
gtggtccgta aagtaactgg t                                                  21

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence:Internal
      Control (IC) Probe
<220> FEATURE:
<221> NAME/KEY: modified_base
<222> LOCATION: (1)
<223> OTHER INFORMATION: n = g modified by quencher (Q) and minor groove
      binder (MGB)
<220> FEATURE:
<221> NAME/KEY: modified_base
<222> LOCATION: (17)
<223> OTHER INFORMATION: n = t modified by "Yakima Yellow" (YY) dye

<400> SEQUENCE: 37
ngcaaagtcc catcgtn                                                       17

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:Eclipse
      probe
<220> FEATURE:
<221> NAME/KEY: modified_base
<222> LOCATION: (1)
<223> OTHER INFORMATION: n = c modified by quencher (Q), trivalent
      linking group (W = -O-(CH-2)-3-N-(CH-2)-2-C(=O)-) and
      minor groove binder (MGB)
```

```
<220> FEATURE:
<221> NAME/KEY: modified_base
<222> LOCATION: (18)
<223> OTHER INFORMATION: n = t modified by linking group (K) and
      6-carboxyfluorescein (FAM)

<400> SEQUENCE: 38
ngtcacaccc gaaggaan                                                      18

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence:Eclipse
      probe
<220> FEATURE:
<221> NAME/KEY: modified_base
<222> LOCATION: (1)
<223> OTHER INFORMATION: n = c modified by quencher (Q), trivalent
      linking group (W = -O-(CH-2)-3-N-(CH-2)-2-C(=O)-) and
      minor groove binder (MGB)
<220> FEATURE:
<221> NAME/KEY: modified_base
<222> LOCATION: (15)
<223> OTHER INFORMATION: n = t modified by linking group (K) and
      fluorophore (Fl)

<400> SEQUENCE: 39
ntcggtcctt gcccn                                                         15

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence:Eclipse
      probe
<220> FEATURE:
<221> NAME/KEY: modified_base
<222> LOCATION: (1)
<223> OTHER INFORMATION: n = c modified by quencher (Q), trivalent
      linking group (W = -O-(CH-2)-3-N-(CH-2)-2-C(=O)-) and
      minor groove binder (MGB)
<220> FEATURE:
<221> NAME/KEY: modified_base
<222> LOCATION: (14)
<223> OTHER INFORMATION: n = g modified by linking group (K) and
      fluorophore (Fl)

<400> SEQUENCE: 40
ngactcggcc cttn                                                          14

<210> SEQ ID NO 41
<211> LENGTH: 13
<212> TYPE: DNA
<213> ORGANISM: Artificial Sequence
<220> FEATURE:
<223> OTHER INFORMATION: Description of Artificial Sequence:Eclipse
      probe
<220> FEATURE:
<221> NAME/KEY: modified_base
<222> LOCATION: (1)
<223> OTHER INFORMATION: n = a modified by quencher (Q), trivalent
      linking group (W = -O-(CH-2)-3-N-(CH-2)-2-C(=O)-) and
      minor groove binder (MGB)
<220> FEATURE:
<221> NAME/KEY: modified_base
<222> LOCATION: (13)
<223> OTHER INFORMATION: n = c modified by linking group (K) and
      fluorophore (Fl)

<400> SEQUENCE: 41
```

-continued

```
nggcgaggaa tan                                              13

<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence:Eclipse
      probe
<220> FEATURE:
<221> NAME/KEY: modified_base
<222> LOCATION: (1)
<223> OTHER INFORMATION: n = a modified by quencher (Q), trivalent
      linking group (W = -O-(CH-2)-3-N-(CH-2)-2-C(=O)-) and
      minor groove binder (MGB)
<220> FEATURE:
<221> NAME/KEY: modified_base
<222> LOCATION: (13)
<223> OTHER INFORMATION: n = c modified by linking group (K) and
      fluorophore (Fl)

<400> SEQUENCE: 42
natcgactcc cgn                                              13

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence:Eclipse
      probe
<220> FEATURE:
<221> NAME/KEY: modified_base
<222> LOCATION: (1)
<223> OTHER INFORMATION: n = a modified by quencher (Q), trivalent
      linking group (W = -O-(CH-2)-3-N-(CH-2)-2-C(=O)-) and
      minor groove binder (MGB)
<220> FEATURE:
<221> NAME/KEY: modified_base
<222> LOCATION: (12)
<223> OTHER INFORMATION: n = c modified by linking group (K) and
      fluorophore (Fl)

<400> SEQUENCE: 43
ntcggctccc gn                                               12
```

REAL-TIME LINEAR DETECTION PROBES: SENSITIVE 5'-MINOR GROOVE BINDER-CONTAINING PROBES FOR PCR ANALYSIS

CROSS-REFERENCES TO RELATED APPLICATIONS

This application is a continuation-in-part of U.S. Ser. No. 09/876,830, filed Jun. 6, 2001, now U.S. Pat. No. 6,790,945 which is a continuation-in part of U.S. Ser. No. 09/457,616, filed Dec. 8, 1999 now U.S. Pat. No. 6,727,356, and claims the benefit of provisional applications U.S. Ser. No. 60/302,137, filed Jun. 29, 2001 and 60/351,637, filed Jan. 23, 2002, the disclosures of each of the above being incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Real time DNA amplification and detection methods are efficient for sequence identification and quantification of a target since no pre-hybridization amplification is required. Amplification and hybridization are combined in a single step and can be performed in a fully automated, large-scale, closed-tube format.

Methods that use hybridization-triggered fluorescent probes for real time PCR are based either on a quench-release fluorescence of a probe digested by DNA Polymerase (e.g., methods using TaqMan, MGB-TaqMan) or on a hybridization-triggered fluorescence of intact probes (e.g., molecular beacons, and linear probes, see U.S. Pat. Nos. 6,030,787, U.S. Pat. No. 5,723,591). In general, the probes are designed to hybridize to an internal region of a PCR product during annealing stage. For those methods utilizing TaqMan and MGB-TaqMan the 5'-exonuclease activity of the approaching DNA Polymerase cleaves a probe between fluorophore and quencher thus releasing fluorescence.

What is needed in the art are new oligonucleotide probes and conjugates that are useful in "real-time" amplification processes and which can be prepared with a variety of nucleotide bases in short lengths. The present invention provides such probes and conjugates, as well as methods for their use.

BRIEF SUMMARY OF THE INVENTION

In one aspect, the present invention provides oligonucleotide probes (or oligonucleotide conjugates, hereinafter "probes/conjugates", "probes" or "conjugates") which are most generally noted as 5'-MGB-Q-ODN-Fl-3' probes or conjugates.

In one group of embodiments, the 5'-MGB-Q-ODN-Fl-3' probe or conjugate has the formula:

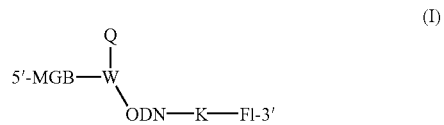

wherein MGB is a minor groove binder, Q is a quencher, W is a trivalent linking group, ODN is an oligonucleotide or modified oligonucleotide, K is a bond or a linking group and Fl is a fluorophore.

In a group of further preferred embodiments, the oligonucleotide probe/conjugate has the formula:

$$\begin{array}{c} Ar^2 \\ | \\ N \\ \| \\ N \\ | \\ Ar^1 \quad [B] \\ | \quad | \\ W-[A]_n-K \\ / \qquad \qquad \backslash \\ MGB \qquad \qquad Fl \\ 5'\text{---------}3' \end{array} \quad (II)$$

in which MGB, W, K and Fl have the meanings provided above, $[A-B]_n$ represents a nucleic acid oligomer (e.g., DNA, RNA, PNA or any combination thereof, including those with modified bases and sugars), wherein A represents a sugar phosphate backbone, modified sugar phosphate backbone, locked nucleic acid backbone, peptidic backbone or a variant thereof used in nucleic acid preparation; and B represents a nucleic acid base, a modified base or a base analog as described in more detail below. The subscript n is an integer of from about 3 to about 100, preferably 6 to about 50 and more preferably 8 to about 20.

Returning to formula II, the symbols $Ar^1$ and $Ar^2$ each represent substituted or unsubstituted aryl groups. In certain preferred embodiments, $Ar^1$ is substituted with one or more electron-donating groups, such as, for example, alkyl, alkoxy, hydroxy, amino, alkylamino, dialkylamino, and the like, and $Ar^2$ is substituted with one or more electron-withdrawing groups, such as, for example, nitro, cyano, carboxy, sulfonyl, halogen, and the like. In still other embodiments, $Ar^2$ is substituted with a group having the formula —U=U—$Ar^3$, wherein each U is independently selected from CH, C(R) and N, in which R is a $(C_1-C_8)$alkyl group and $Ar^3$ is a substituted or unsubstituted aryl group. Preferred aryl groups for each of $Ar^1$, $Ar^2$ and $Ar^3$ are phenyl groups.

In still further preferred embodiments, the oligonucleotide probe/conjugate has a formula selected from:

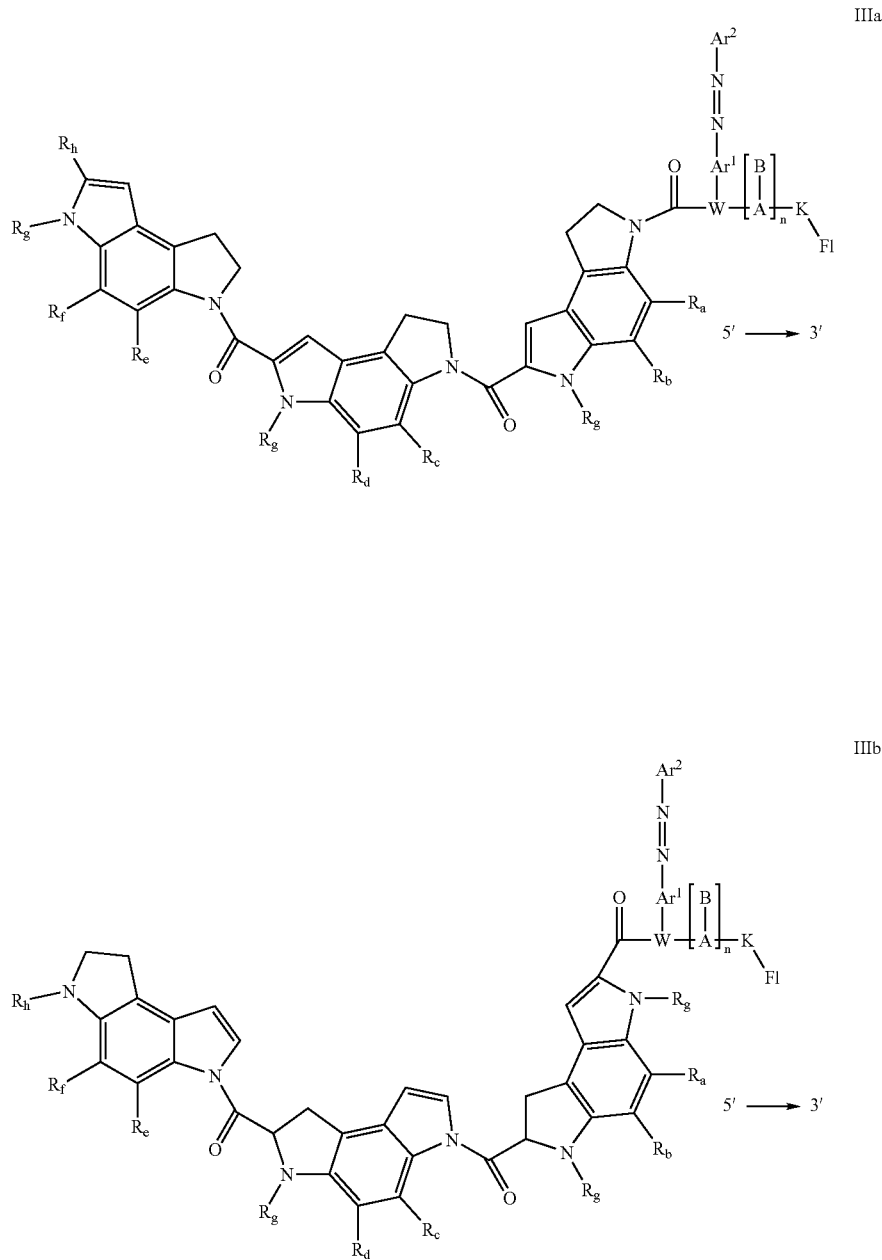

in which Ar$^1$, Ar$^2$, W, K, Fl, A, B and the subscript n have the meanings provided above, and wherein the symbols R$_a$, R$_b$, R$_c$, R$_d$, R$_e$ and R$_f$ represent substituents selected from H, halogen, (C$_1$–C$_8$)alkyl, OR$_g$, N(R$_g$)$_2$, N$^+$(R$_g$)$_3$, SR$_g$, COR$_g$, CO$_2$R$_g$, CON(R$_g$)$_2$, (CH$_2$)$_m$SO$_3^-$, (CH$_2$)$_m$CO$_2^-$, (CH$_2$)$_m$OPO$_3^{-2}$, and NHC(O)(CH$_2$)$_m$CO$_2^-$, and esters and salts thereof, wherein each R$_g$ is independently H or (C$_1$–C$_8$) alkyl, and the subscript m is an integer of from 0 to 6. The symbol R$_h$ represents H or a group (typically the vestige of a linking group used in solid phase synthesis) having from 1–30 atoms selected from C, N, O, P, and S which is either cyclic, acyclic, or a combination thereof, and having additional hydrogen atoms to fill the available valences.

In still further preferred embodiments, the oligonucleotide probe/conjugate has the formula:

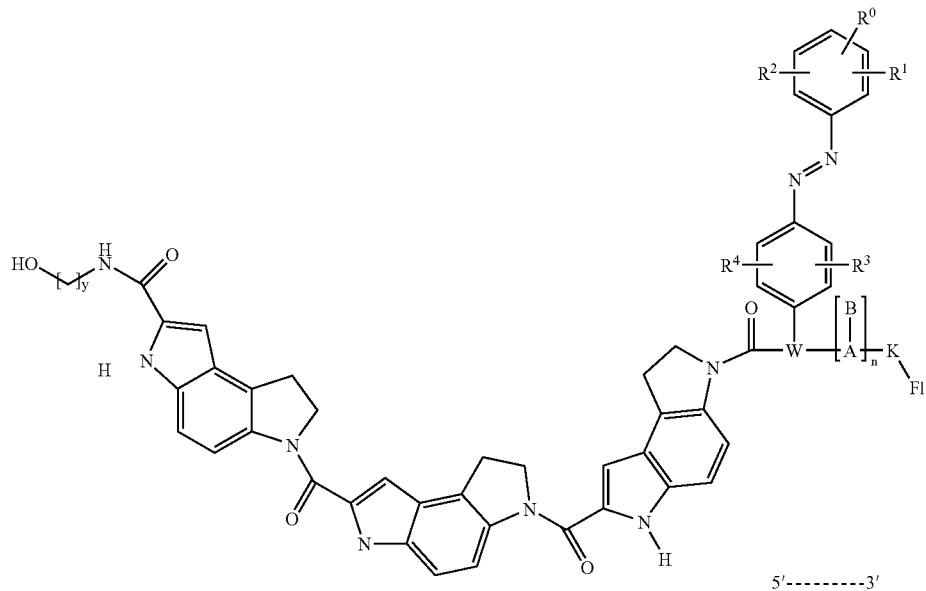

in which W, K, Fl, A, B and the subscript n have the meanings provided above, and wherein the symbols $R^0$, $R^1$ and $R^2$ represent H or electron-withdrawing groups, the symbols $R^3$ and $R^4$ represent H or electron-donating groups, and the subscript m is an integer of from 1 to 20. In a particularly preferred embodiment, W is —$(CH_2)_3N(-)$—$(CH_2)_3$—; $R^0=NO_2$; $R^1=Cl$; $R^2=R^3=R^4=H$; K is a ($C_1$–$C_6$) alkylene linker and y=5.

The probes or conjugates provided above have utility, particularly in real time PCR amplification processes.

Accordingly, the present invention further provides a method for continuous monitoring of polynucleotide amplification, comprising:

(a) combining a sample containing a target sequence, with one or more oligonucleotide primers complementary to regions of the target sequence, a polymerizing enzyme, nucleotide substrates, and an oligonucleotide conjugate having a formula:

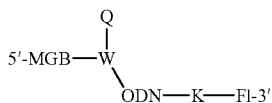

wherein MGB is a minor groove binder, Q is a quencher, W is a trivalent linking group, ODN is an oligonucleotide or modified oligonucleotide, K is a bond or a linking group and Fl is a fluorophore, and the ODN portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

In a related aspect, the present invention provides a method for monitoring gene expression comprising:

(a) providing an array of oligonucleotide probes of different sequences, (b) incubating a population of polynucleotides with the array under hybridization conditions, and (c) determining to which of the oligonucleotide probes in the array the population hybridizes;

wherein one or more of the oligonucleotide probes has the formula:

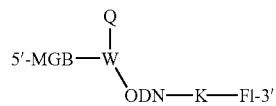

wherein MGB is a minor groove binder, Q is a quencher, W is a trivalent linking group, ODN is an oligonucleotide or modified oligonucleotide, K is a bond or a linking group and Fl is a fluorophore.

In still another aspect, the present invention provides a method for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising:

(a) contacting the mixture of polynucleotides with an oligonucleotide conjugate having the formula:

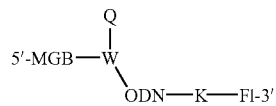

wherein MGB is a minor groove binder, Q is a quencher, W is a trivalent linking group, ODN is an oligonucleotide or modified oligonucleotide, K is a bond or a linking group and Fl is a fluorophore; and wherein the conjugate forms a stable hybrid only with said target sequence that is perfectly complementary to the ODN portion of said conjugate, and the conjugate does not form a stable hybrid with any of the other polynucleotides; and
  (b) measuring the fluorescence produced on hybrid formation, whereby hybrid formation indicates the presence of said target sequence.

In yet another aspect, the present invention provides a method for distinguishing between wild-type, mutant and heterozygous target polynucleotides, said method comprising:
  (a) contacting a sample containing a target polynucleotide with two probes wherein a first probe is specific for said wild-type target polynucleotide and a second probe is specific for said mutant target polynucleotide, each of said probes having a formula:

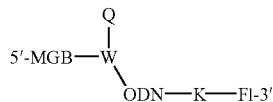

wherein MGB is a minor groove binder, Q is a quencher, W is a trivalent linking group, ODN is an oligonucleotide or modified oligonucleotide, K is a bond or a linking group and Fl is a fluorophore; wherein said first and second probes have different fluorophores and each of said probes forms a stable hybrid only with the target sequence that is perfectly complementary to the ODN portion of said probes; and
  (b) measuring the fluorescence produced on hybrid formation, whereby hybrid formation indicates the presence or absence of each of said wild-type, mutant and heterozygous target polynucleotides.

In addition to the above, the present invention fuirther provides probe kits, containing one or more primers, preferably those having modified bases that can be used for AT-rich sequences, or for G-rich sequences (three or more Gs in a row) and one or more probes having the formulae provided above.

DETAILED DESCRIPTION OF THE INVENTION

Definitions

Figure 1:
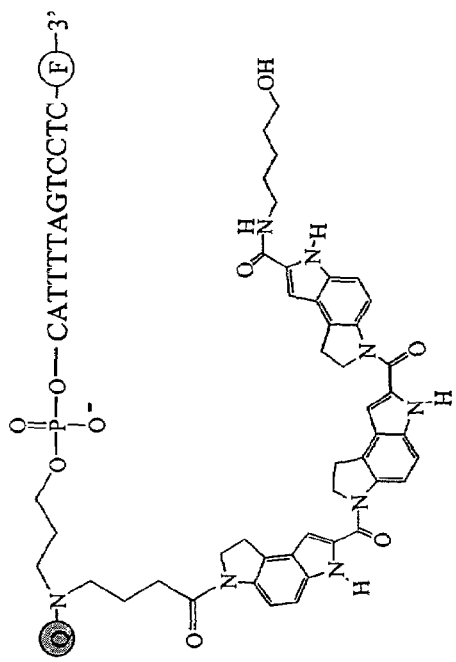
FIG. 1 illustrates a) the structure of a 5'-MGB-Q-ODN-Fl conjugate (SEQ ID NO:1) and b) the detection of DNA target by a 5'-MGB-Q-ODN-Fl probe, wherein the probe is not digested.

In the reaction schemes and description below (and above), the abbreviations MGB, FL, Q, CPG and ODN refer to "minor groove binder", "fluorescent label" or "fluorophor", "quencher", "controlled pore glass" (as an example of a solid support) and "oligonucleotide" moieties or molecules, respectively, and in a manner which is apparent from context. In certain formulae, the group [A—B]$_n$ is used to refer to an oligonucleotide, modified oligonucleotide or peptide-nucleic acid having 'n' bases (B) and being linked along a backbone of 'n' sugars, modified sugars or amino acids (A). The terms "probe" and "conjugate" are used interchangeably and refer to an oligonucleotide having an attached minor groove binder, fluorophore and quencher.

Unless otherwise stated, the following terms used in the specification and claims have the meanings given below:

The terms "fluorescent label" or "fluorophore" refers to compounds with a fluorescent emission maximum between about 400 and 900 nm. These compounds include, with their emission maxima in nm in brackets, Cy2™ (506), GFP (Red Shifted) (507), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO®-1 (533), JOE (548), BODIPY® 530/550 (550), DiI (565), BODIPY® TMR (568), BODIPY® 558/568 (568), BODIPY® 564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO™-3 (631), R-phycocyanin (642), C-Phycocyanin (648), TO-PRO™-3 (660), TOTO®-3 (660), DiD DilC(5) (665), Cy5™ (670Thiadicarbocyanine (671), Cy5.5 (694).

The term "linker" refers to a moiety that is used to assemble various portions of the molecule or to covalently attach the molecule (or portions thereof) to a solid support. Typically a linker or linking group has functional groups that are used to interact with and form covalent bonds with functional groups in the ligands or components (e.g., fluorophores, oligonucleotides, minor groove binders, or quenchers) of the conjugates described and used herein. Examples of finctional groups on the linking groups (prior to interaction with other components) include —$NH_2$, —$NHNH_2$, —$ONH_2$, —NHC=(O)$NHNH_2$, —OH, or —SH. The linking groups are also those portions of the molecule that connect other groups (e.g., phosphoramidite moieties and the like) to the conjugate. Additionally, a linker can include linear or acyclic portions, cyclic portions, aromatic rings or combinations thereof.

The term "solid support" refers to any support that is compatible with oligonucleotides synthesis, including, for example, glass, controlled pore glass, polymeric materials, polystyrene, beads, coated glass and the like.

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, ($C_1$–$C_8$)alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, ($C_1$–$C_6$)alkylene is meant to include methylene, ethylene, propylene, 2-methylpropylene, pentylene, and the like.

The term "aryl" means a monovalent or bivalent (e.g., arylene) monocyclic or bicyclic aromatic hydrocarbon radical of 6 to 10 ring atoms which is unsubstituted or substituted independently with one to four substituents, preferably one, two, or three substituents selected from those groups provided below. Ther term "aryl" is also meant to include those groups described above wherein one or more heteroatoms or heteroatom functional groups have replaced a ring carbon, while retaining aromatic properties, e.g., pyridyl, quinolinyl, quinazolinyl, thienyl, and the like. More specifically the term aryl includes, but is not limited to, phenyl, 1-naphthyl, 2-naphthyl, thienyl and benzothiazolyl, and the substituted forms thereof.

Substituents for the aryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R'" are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl. Still further, one of the aryl rings (Ar$^1$ and Ar$^2$, below) can be further substituted with another substituted aryl group to extend the resonance ability of the aromatic system, directly or indirectly through groups such as —(CR'=CR')$_n$— and —(C≡C)$_n$—, where n is 0 to 5, increasing the wavelength absorbance maximum.

The prefix "halo" and the term "halogen" when used to describe a substituent, refer to —F, —Cl, —Br and —I.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic finctionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of "Advanced Organic Chemistry", 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g, $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Futs, Protective Groups in Organic Chemistry, (Wiley, 2nd ed. 1991) and Harrison and Harrison et al., Compendium of Synthetic Organic Methods, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. In general, the preferred protecting groups are those that can be removed under acidic conditions or basic conditions, or those groups that can be removed by the use of a particular light source (e.g., "light sensitive" protecting groups). Additionally, selection of an appropriate protecting group is made with due consideration to other fuinctionality in the molecule so that either the incorporation or removal of the protecting group does not interfere or otherwise significantly affect the remainder of the molecule.

"Optional" or "optionally" in the above definitions means that the subsequently described event or circumstance may but need not occur, and that the description includes instances where the event or circumstance occurs and instances in which it does not. For example, "aryl optionally mono- or di- substituted with an alkyl group" means that the alkyl group may, but need not, be present, and the description includes situations where the aryl group is mono- or disubstituted with an alkyl group and situations where the aryl group is not substituted with the alkyl group.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

The term "Eclipse™ probe" refers, in general, to a 5'-MGB-Q-ODN-Fl probe. In contrast, a "TaqMan® MGB™ probe refers to a 3'-MGB-Q-ODN-Fl probe. Eclipse™ and MGB™ are trademarks of Epoch Biosciences, Inc., Bothell, Wash.; and TaqMan® is a registered trademark of Applied Biosystems, Inc., Foster City, Calif.

General

Minor groove binder oligonucleotide conjugates (or "probes") have recently been described (see WO 99/51621). These conjugates form hyper-stabilized duplexes with complementary DNA. In particular, sequence specificity of short MGB probes is excellent for high temperature applications such as PCR. Quite surprisingly, probes containing a minor groove binding-quencher compound at the 5'-end and a fluorophore at the 3'-end are particularly useful for assay methods using fluorogenic 2'-deoxynucleotides. These probes fluoresce upon hybridization to the complementary target. The 5'-MGB-quencher group has now been found to prevent 5'-nuclease digestion by Taq polymerase during homogeneous amplification. Moreover, the 5'-MGB-quencher-oligonucleotide-fluorophore (5'-MGB-Q-ODN-Fl) probes described herein display a dynamic range of 7 orders of magnitude, with an ultimate sensitivity of better than 5 copies per sample in real-time PCR amplification reactions. An example of a 5'-MGB-Q-ODN-Fl conjugate is shown in FIG. 1A. On hybridization to a target, the probe fluoresces as shown in FIG. 1B.

The probe/conjugates of the present invention are constructed such that the probe exists in at least one single-stranded conformation when unhybridized. In the unhybridized random coil form the quencher is near enough to the fluorophore to quench the fluorescence of the fluorophore. When hybridized to a target polynucleotide, the probe/conjugate adopts a conformation such that the quencher is not positioned close enough to the fluorophore to quench its fluorescence. By adopting these hybridized and unhybridized conformations, the fluorophore and quencher portions of the probe exhibit different fluorescence signal intensities when the probe is hybridized and unhybridized. As a result, it is possible to determine whether the probe is hybridized or unhybridized based on a change in the fluorescence intensity of the probe, and the use of such probes allow the monitoring of DNA amplification reactions.

The minor groove binder-quencher-oligonucleotide-fluorophore conjugates of the present invention can be in a linear arrangement (as suggested by the formula 5'-MGB-Q-ODN-Fl-3') or in a branched arrangement wherein the quencher (Q) and the minor groove binder (MGB) are attached to a linking group that serves to join ODN, Q and MGB. Additionally, the quencher can be attached at the distal (relative to attachment to ODN) terminus of the minor groove binder (e.g., 5'-Q-MGB-ODN-Fl). Each of the arrangements are meant to be included when the linear abbreviation (MGB- Q-ODN-Fl) is used. Additionally, while the MGB and Q portions are attached at the 5' end of the oligonucleotide, the fluorophore portion can be attached at the 3' end, or an internal position of the oligonucleotide, so long as such attachment does not interfere with the quenching mechanisms of the conjugate. Generally, this can be accomplished through the use of a suitable linking group (see Examples below). As a result, the present invention provides a number of preferred embodiments in which linkages between ODN and Fl are selected to provide suitable separation distances between the quencher and fluorophore moieties, while not compromising the hybridization capabilities of the oligonucleotide portion.

As noted above, the conjugates of the present invention are useful in a variety of hybridization-based detection assays, but find particular utility in "real-time" detection of oligonucleotide amplification, often conducted via PCR.

Figure 2:
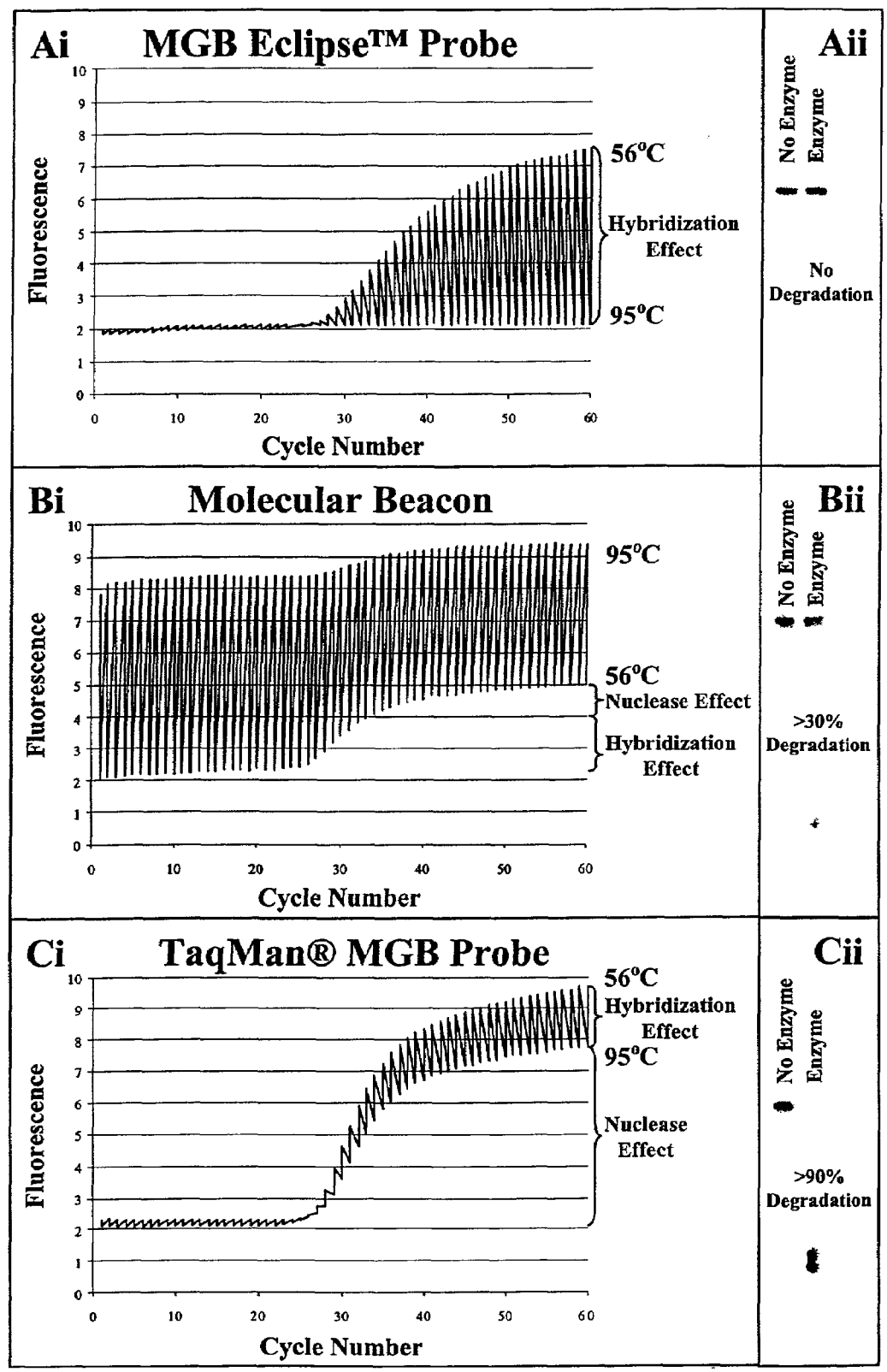
FIG. 2 illustrates the fluorescent behavior and 5'-nuclease resistance of MGB Eclipse™ (A), Molecular Beacon (B) and TaqMan® MGB (C) probes. Real time PCRs were performed with RRM1 primers and MGB Eclipse™ (A, i), Molecular Beacon (B, i), and TaqMan® MGB (C, i) FAM-labeled or $^{32}$P-labeled probes (A, ii; B, ii; C, ii.in Light Cycler as described with human "66 son" Pedigree DNA as a template in Light Cycler (Idaho Technology). Fluorescent readings were taken at denaturing step (95° C.) and annealing step (56° C.) of the reaction. Control reactions for radioactive probes did not have Taq Polymerase (no enzyme lanes). After completion of the PCR radioactive reactions were subjected to electrophoresis, autoradiographed and analyzed on a phosphoimager. Respective images are placed to the right of the real time fluorescent plots.

FIG. 2 illustrates the fluorescent behavior and 5'-nuclease resistance of MGB Eclipse™ (A), Molecular Beacon (B) and TaqMan® MGB (C) probes. Fluorogenic probes used in real time PCR rely upon the detection and quantification of a fluorescent reporter, the signal of which increases due to a release of quenching caused by an event occurring as a result of, and in direct proportion to, the amount of PCR product in a reaction. FIG. 2 illustrates the distinct patterns of fluorescent signals generated from three different fluorogenic probes during PCR. PCR was conducted in Light Cycler using RRM1 specific primers (see Table 5 in Example 2) and fluorogenic probes (MGB Eclipse™ probe, Molecular Beacon, or TaqMan® MGB). Each reaction began with 10 ng of "66 son" human genomic DNA as a template in a 10 μL reaction. Fluorescent measurements were taken at denaturing and annealing steps.

Fluorescence of the MGB Eclipse™ probe taken at the denaturing temperature is low and does not increase during PCR (FIG. 2, Ai), indicating absence of probe digestion. The 5'-MGB-Q moiety effectively blocks nuclease digestion by Taq DNA polymerase. The fluorescence of the MGB Eclipse™ probe, measured during the annealing step of PCR, increases with time, indicative of the growing amount of target amplicon to which the MGB Eclipse™ probes hybridize.

Molecular Beacons, like MGB Eclipse™ probes, are designed to remain intact during the amplification reaction, and rebind to target in every cycle for signal measurement. Fluorescence of the Molecular Beacon, taken at the denaturing temperature, is high and increases about 20% during PCR, indicating partial digestion of the probe. This "nuclease effect" depends on the probe sequence and conditions of the PCR, and usually accounts for 10%–40% of the total signal. Molecular Beacon fluorescence measured during annealing step of the PCR increases with time in accordance with PCR product amount (FIG. 2, Bi). The fluorescent background of the MGB Eclipse™ probes is significantly lower than, and the signal to noise ratio comparable to, the much longer Molecular Beacon probes.

The fluorescence pattern of the TaqMan® MGB probe is different from the previous two probes (FIG. 2, Ci). At the initial steps of the PCR when there is no product to hybridize to, fluorescence of the probe is low at both 56° and 95° C. This is typical for all short MGB probes. With PCR progression nuclease digestion leads to signal accumulation and fluorescence increase at both temperatures. At the last cycles of PCR there is evidence of a "hybridization fluorescence effect" in the behavior of a TaqMan® MGB probe: fluorescence at 56° C. is higher than at 95° C. Presumably the undigested fraction of the probe behaves like hybridization probes that fluoresce upon hybridization.

Description of the Embodiments

Probes and Conjugates

In one aspect, the present invention provides oligonucleotide probes (or oligonucleotide conjugates, hereinafter "probes/conjugates", "probes" or "conjugates") which are most generally noted as 5'-MGB-Q-ODN-Fl-3' probes or conjugates. As noted above, this linear depiction of the probes is meant to indicate that a minor groove binder and a quencher or quenching agent are attached to the 5' end of the oligonucleotide portion, and a fluorophore is attached to the 3' end of the oligonucleotide portion. For any of these covalently attached portions, connection can be either direct or via a linking group. In some embodiments, linking groups are preferred to provide sufficient spacing between interactive portions (e.g., fluorophore and quencher) or reactive portions (e.g., minor groove binders that are meant to bind non-covalently in the minor groove formed by probe hybridization to a target sequence).

Accordingly, in one group of embodiments, the 5'-MGB-Q-ODN-Fl-3' probe or conjugate has the formula:

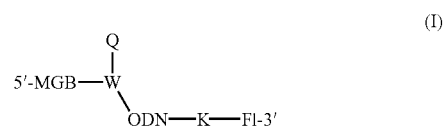

(I)

wherein MGB is a minor groove binder, Q is a quencher, W is a trivalent linking group, ODN is an oligonucleotide or modified oligonucleotide, K is a bond or a linking group and Fl is a fluorophore.

More particularly, when K is a linking group, it will generally have from 1 to 30 main chain atoms (counting only those atoms between the ODN component and the Fl component that are joined in a continuous line, including all ring atoms, but not including any pendant atoms or groups) that are selected from C, O, N, S, P and Si. The linking group W will generally represent a trivalent linker having from about 3 to 100 main chain atoms, selected from C, O, N, S, P and Si. Additionally, W can contain a branched aliphatic chain, a heteroalkyl chain, one or more substituted ring structures, or combinations thereof. In some embodiments, W represents a trifunctional moiety such as an amino group with or without pendent functionalized linking groups such that Q-W represents a quencher from, for example, commercial sources (see Table 1 of quenchers below). Accordingly, while W is provided as a linking group, it will in some embodiments be an amino group that may be considered a part of Q. Each of the linking groups, as well as other components, will be discussed in more detail below.

In a group of further preferred embodiments, the oligonucleotide probe/conjugate has the formula:

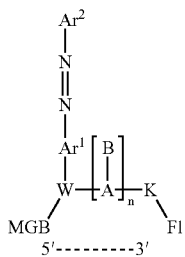
(II)

in which MGB, W, K and Fl have the meanings provided above, [A—B]$_n$ represents a nucleic acid oligomer (e.g., DNA, RNA, PNA or any combination thereof, including those with modified bases and sugars), wherein A represents a sugar phoshpate backbone, modified sugar phosphate backbone, locked nucleic acid backbone, peptidic backbone or a variant thereof used in nucleic acid preparation; and B represents a nucleic acid base, a modified base or a base analog as described in more detail below. The subscript n is an integer of from about 3 to about 100, preferably 6 to about 50 and more preferably 8 to about 25.

Returning to formula II, the symbols Ar$^1$ and Ar$^2$ each represent substituted or unsubstituted aryl groups. In certain preferred embodiments, Ar$^1$ is substituted with one or more electron-donating groups, such as, for example, alkyl, alkoxy, hydroxy, amino, alkylamino, dialkylamino, and the like, and Ar$^2$ is substituted with one or more electron-withdrawing groups, such as, for example, nitro, cyano, carboxy, sulfonyl, halogen, and the like. In still other embodiments, Ar$^2$ is substituted with a group having the formula —U═U—Ar$^3$, wherein each U is independently selected from CH, C(R) and N, in which R is a (C$_1$–C$_8$)alkyl group and Ar$^3$ is a substituted or unsubstituted aryl group. Preferred aryl groups for each of Ar$^1$, Ar$^2$ and Ar$^3$ are phenyl groups.

In still further preferred embodiments, the oligonucleotide probe/conjugate has the formula:

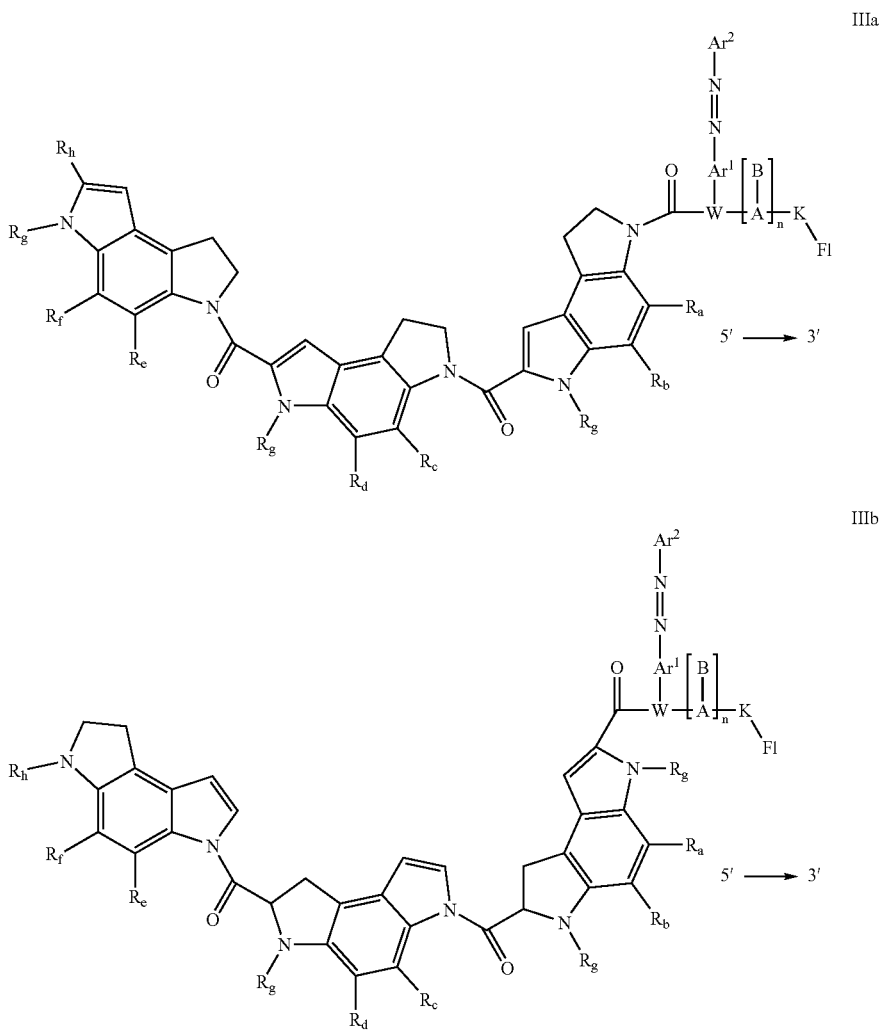

in which $Ar^1$, $Ar^2$, W, K, Fl, A, B and the subscript n have the meanings provided above, and wherein the symbols $R_a$, $R_b$, $R_c$, $R_d$, $R_e$ and $R_f$ represent substituents selected from H, halogen, $(C_1-C_8)$alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)_mCO_2^-$, $(CH_2)_mOPO_3^{-2}$, and $NHC(O)(CH_2)_mCO_2^-$, and esters and salts thereof, wherein each $R_g$ is independently H or $(C_1-C_8)$ alkyl, and the subscript m is an integer of from 0 to 6. The symbol $R_h$ represents H or a group (typically the vestige of a linking group used in solid phase synthesis) having from 1–30 atoms selected from C, N, O, P, and S which is either cyclic, acyclic, or a combination thereof, and having additional hydrogen atoms to fill the available valences.

In still further preferred embodiments, the oligonucleotide probe/conjugate has the formula:

is selected to have three or more consecutive guanine bases wherein at least one of the guanine bases is replaced with a modified base, preferably PPG. Still more preferably, the ODN portion is a RNA, a chimera, a PNA or a locked nucleic acid.

Still other preferred probes or conjugates are those in each of formulae I, II, IIa and IIIb, and IV wherein the ODN portion is selected to be complementary to a target sequence having 30% or more A and T bases, wherein the ODN contains at least one modified base sufficient to provide an increase in stability of the duplex (probe/target hybrid) of at least about 3° C. More preferably, the ODN portion is selected to be complementary to a target sequence having 50% or more A and T bases, wherein the ODN contains sufficient modified bases to provide an increase in stability

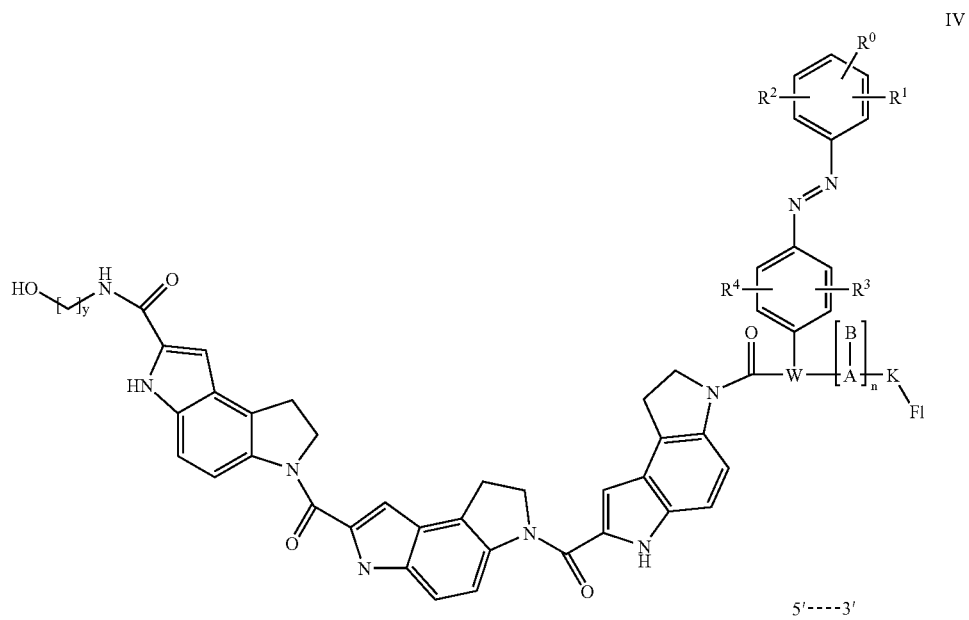

IV in which W, K, Fl, A, B and the subscript n have the meanings provided above, and wherein the symbols $R^0$, $R^1$ and $R^2$ represent H or electron-withdrawing groups, the symbols $R^3$ and $R^4$ represent H or electron-donating groups, and the subscript m is an integer of from 1 to 20. In a particularly preferred embodiment, W is —$(CH_2)_3N(-)$—$(CH_2)_3$—; $R^0=NO_2$; $R^1=Cl$; $R^2=R^3=R^4=H$; K is a $(C_1-C_6)$ alkylene linker and y=5.

In certain preferred embodiments for each of the above groups, K is selected to provide particular fluorescence enhancement for the probe/conjugate, and will depend on the length of the oligonucleotide portion of the probe. Accordingly, for probes having 18 or more nucleotides (including modified nucleotides or analogs), K can be a bond or a linking group up to about 20 atoms in length. More preferably, K is a polyalkylene glycol linker or a ribose or deoxy ribose linker (discussed in more detail below). In particularly preferred embodiments, K is a polyalkylene glycol linker such as a polyethylene glycol, polypropylene glycol or polybutylene glycol linker. Most preferred are the polyethylene glycol and functionalized polyethylene glycol linkers that can be obtained from commercial sources.

Other preferred probes or conjugates are those in each of formulae I, II, III and IIIb, and IV wherein the ODN portion of the duplex (probe/target hybrid) of at least about 5° C. Still more preferably, the ODN portion is a RNA, a chimera, a PNA or a locked nucleic acid.

The probes and conjugates of the present invention are generally prepared using solid phase methods known to those of skill in the art. Assembly can be carried out in either the 5' to 3' direction, or the 3' to 5' direction, using, for example, appropriate phosphoramidite reagents for coupling the ODN monomers, the fluorophores, quenchers and minor groove binders. Other methods for assembly include well known functional group condensations to prepare, for example, ester linkages, amide linkages, disulfide linkages, ether linkages, thioether linkages, and the like. In general, the starting materials are commercially available, or can be prepared in a straightforward manner from commercially available starting materials, using suitable functional group manipulations as described in, for example, March, et al., ADVANCED ORGANIC CHEMISTRY—Reactions, Mechanisms and Structures, 4th ed., John Wiley & Sons, New York, N.Y., (1992).

Returning to the more general provisions for the probes/conjugates of the present invention, the discussion below illustrates the types of oligonucleotides, quenching agents or quenchers, minor groove binders, fluorophores and linking groups that can be used herein.

Oligonucleotides and Modified Oligonucleotides

The terms oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids which are disclosed by Nielsen et al. *Science* 254:1497–1500 (1991); bicyclo DNA oligomers (Bolli et al., *Nucleic Acids Res*. 24:4660–4667 (1996)) and related structures. For the conjugates of the present invention, a MGB moiety and a quenching agent are attached at the 5' end of the oligomer and a fluorophore or fluorescent label is attached at the 3' end or in an internal portion of the oligomer.

Preferred in the present invention are DNA oligonucleotides that are single-stranded and have a length of 100 nucleotides or less, more preferably 50 nucleotides or less, still more preferably 30 nucleotides or less and most preferably 20 nucleotides or less with a lower limit being approximately 5 nucleotides.

Oligonucleotide conjugates containing a fluorophore/quencher pair with a minor groove binder may also comprise one or more modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7-deazapurines and their derivatives and pyrazolopyrimidines (described in PCT WO 90/14353); and also described in U.S. Pat. No. 6,127,121.

The most preferred modified bases for use in the present invention include the guanine analogue 6-amino-1H-pyrazolo[3,4-d]pyrimidin-4(5H)-one (ppG or PPG, also Super G) and the adenine analogue 4-amino-1H-pyrazolo[3,4-d] pyrimidine (ppA or PPA). The xanthine analogue 1H-pyrazolo[5,4-d]pyrimidin-4(5H)-6(7H)-dione (ppX) can also be used. These base analogues, when present in an oligonucleotide, strengthen hybridization and improve mismatch discrimination. All tautomeric forms of naturally-occurring bases, modified bases and base analogues may be included in the oligonucleotide conjugates of the invention. Other modified bases useful in the present invention include 6-amino-3-prop-1-ynyl-5-hydropyrazolo[3,4-d]pyrimidine-4-one, PPPG; 6-amino-3-(3-hydroxyprop-1-yny)1–5-hydro-pyrazolo[3,4-d]pyrimidine-4-one, HOPPPG; 6-amino-3-(3-aminoprop-1-ynyl)-5-hydropyrazolo[3,4-d]pyrimidine-4-one, NH$_2$PPPG; 4-amino-3-(prop-1-ynyl)pyrazolo[3,4-d] pyrimidine, PPPA; 4-amino-3-(3-hydroxyprop-1-ynyl) pyrazolo[3,4-d]pyrimidine, HOPPPA; 4-amino-3-(3-aminoprop-1-ynyl)pyrazolo[3,4-d]pyrimidine, NH$_2$PPPA; 3-prop-1-ynylpyrazolo[3,4-d]pyrimidine-4,6-diamino, (NH$_2$)$_2$PPPA; 2-(4,6-diaminopyrazolo[3,4-d]pyrimidin-3-yl)ethyn-1-ol, (NH$_2$)$_2$PPPAOH; 3-(2-aminoethynyl)pyrazolo[3,4-d]pyrimidine-4,6-diamine, (NH$_2$)$_2$PPPANH$_2$; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1, 3-dihydropyrimidine-2-one, NH$_2$PC; 5-[4-amino-3-(3-methoxyprop-1-ynyl)pyrazol[3,4-d]pyrimidinyl]-2-(hydroxymethyl)oxolan-3-ol, CH$_3$OPPPA; 6-amino-1-[4-hydroxy-5-(hydroxymethyl)oxolan-2-yl]-3-(3-methoxyprop-1-ynyl)-5-hydropyrazolo[3,4-d]pyrimidin-4-one, CH$_3$OPPPG; 4,(4,6-Diamino-1H-pyrazolo[3,4-d] pyrimidin-3-yl)-but-3-yn-1-ol, Super A; 6-Amnino-3-(4-hydroxy-but-1-ynyl)-1,5-dihydro-pyrazolo[3,4-d] pyrimidin-4-one; 5-(4-hydroxy-but-1-ynyl)-1H-pyrimidine-2,4-dione, Super T; 3-iodo-1H-pyrazolo[3,4-d]pyrimidine-4,6-diamine ((NH$_2$)$_2$PPAI); 3-bromo-1H-pyrazolo[3,4-d] pyrimidine-4,6-diamine ((NH$_2$)$_2$PPABr); 3-chloro-1H-pyrazolo[3,4-d]pyrimidine-4,6-diamine ((NH$_2$)$_2$PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl).

In addition to the modified bases noted above, the oligonucleotides of the invention can have a backbone of sugar or glycosidic moieties, preferably 2-deoxyribofuranosides wherein all internucleotide linkages are the naturally occurring phosphodiester linkages. In alternative embodiments however, the 2-deoxy-β-D-ribofuranose groups are replaced with other sugars, for example, β-D-ribofuranose. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Related oligomer-forming sugars useful in the present invention are those that are "locked", i.e., contain a methylene bridge between C-4' and an oxygen atom at C-2'. Other sugar moieties compatible with hybridization of the oligonucleotide can also be used, and are known to those of skill in the art, including, but not limited to, α-D-arabinofuranosides, α-2'-deoxyribofuranosides or 2',3'-dideoxy-3'-aminoribofuranosides. Oligonucleotides containing α-D-arabinofuranosides can be prepared as described in U.S. Pat. No. 5,177,196. Oligonucleotides containing 2',3'-dideoxy-3'-aminoribofuranosides are described in Chen et al. *Nucleic Acids Res*. 23:2661–2668 (1995). Synthetic procedures for locked nucleic acids (Singh et al, *Chem. Comm*., 455–456 (1998); Wengel J., *Acc. Chem. Res*., 32:301–310 (1998)) and oligonucleotides containing 2'-halogen-2'-deoxyribofuranosides (Palissa et al., *Z. Chem*. 27:216 (1987)) have also been described. The phosphate backbone of the modified oligonucleotides described herein can also be modified so that the oligonucleotides contain phosphorothioate linkages and/or methylphosphonates and/or phosphoroamidates (Chen et al., *Nucl Acids Res*., 23:2662–2668 (1995)). Combinations of oligonucleotide linkages are also within the scope of the present invention. Still other backbone modifications are known to those of skill in the art.

In another group of embodiments, the modified bases described herein are incorporated into PNA and DNA/PNA chimeras to balance $T_m$s and provide modified oligonucleotides having improved mismatch discrimination. Various modified forms of DNA and DNA analogues have been used in attempts to overcome some of the disadvantages of the use of DNA molecules as probes and primers. Among these are peptide nucleic acids (PNAs, also known as polyamide nucleic acids). Nielsen et al. *Science* 254:1497–1500 (1991). PNAs contain heterocyclic base units, as found in DNA and RNA, that are linked by a polyamide backbone, instead of the sugar-phosphate backbone characteristic of DNA and RNA. PNAs are capable of hybridization to complementary DNA and RNA target sequences and, in fact, hybridize more strongly than a corresponding nucleic acid probe. The synthesis of PNA oligomers and reactive monomers used in the synthesis of PNA oligomers have been described in U.S. Pat. Nos. 5,539,082; 5,714,331; 5,773,571; 5,736,336 and 5,766,855. Alternate approaches to PNA and DNA/PNA chimera synthesis and monomers for PNA synthesis have been summarized. Uhlmann et al. *Angew. Chem. Int. Ed.* 37:2796–2823 (1998). Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases, sugar modification, backbone modification or a minor groove binder to balance the $T_m$ of a DNA, PNA or DNA/PNA chimera is in the scope of this invention. The synthetic methods necessary for the synthesis of modified base monomeric units required for nucleic acid, PNA and PNA/DNA chimeras synthesis are available in the art, see methods in this application and Uhlmann et al. *Angew. Chem. Int. Ed.* 37:2796–2823 (1998).

For the uses described herein, and as noted above, the oligonucleotides and modified oligonucleotides will preferably have from 5 to 100 bases, more preferably from 5 to 50 bases, still more preferably, 5 to 30 bases, and even more preferably, 5 to 20 bases. In some embodiments, the oligonucleotide portions of the probes/conjugates will have 5 to 15 bases. In some embodiments, the oligonucleotide portions will have 6, 7, 8, 9, 10, 11, 12, 13 or 14 bases or modified bases.

The ability to design probes and primers in a predictable manner using an algorithm, that can direct the use or incorporation of modified bases, minor groove binders, fluorphores and/or quenchers, based on their thermodynamic properties have been described in co-pending application Ser. No. 10/032,307, filed Dec. 21, 2001. Accordingly, the use of any combination of normal bases, unsubstituted pyrazolo[3,4-d]pyrimidine bases (e.g., PPG and PPA), 3-substituted pyrazolo[3,4-d]pyrimidines, modified purine, modified pyrimidine, 5-substituted pyrimidines, universal bases, sugar modification, backbone modification or a minor groove binder to balance the $T_m$ (e.g., within about 5–8° C.) of a hybridized product with a nucleic acid, PNA or DNA/PNA chimera is contemplated by the present invention.

Minor Groove Binders

The probes/conjugates of the present invention will also have a covalently attached minor groove binder (MGB). A variety of suitable minor groove binders have been described in the literature. See, for example, Kutyavin, et al. U.S. Pat. No. 5,801,155; Wemmer, D. E., and Dervan P. B., *Current Opinon in Structural Biology*, 7:355–361 (1997); Walker, W. L., Kopka, J. L. and Goodsell, D. S., *Biopolymers*, 44:323–334 (1997); Zimmer, C & Wahnert, U. *Prog. Biophys. Molec. Bio.* 47:31–112 (1986) and Reddy, B. S. P., Dondhi, S. M., and Lown, J. W., *Pharmacol. Therap.*, 84:1–111 (1999).

Suitable methods for attaching MGBs (as well as reporter groups such as fluorophores and quenchers described below) through linkers to oligonucleotides are described in, for example, U.S. Pat. Nos. 5,512,677; 5,419,966; 5,696,251; 5,585,481; 5,942,610 and 5,736,626.

The MGB is generally attached to the 5' position of the oligonucleotide portion via a suitable linking group. Attachment at the 5' end provides both a benefit of hybrid stability, since melting of an oligonucleotide duplex begins at the termini, but also reduces and/or prevent nuclease digestion of the probe during amplification reactions.

The location of a MGB within a MGB-oligonucleotide conjugate can also affect the discriminatory properties of such a conjugate. An unpaired region within a duplex will result in changes in the shape of the minor groove in the vicinity of the mispaired base(s). Since MGBs fit best within the minor groove of a perfectly-matched DNA duplex, mismatches resulting in shape changes in the minor groove would reduce binding strength of a MGB to a region containing a mismatch. Hence, the ability of a MGB to stabilize such a hybrid would be decreased, thereby increasing the ability of a MGB-oligonucleotide conjugate to discriminate a mismatch from a perfectly-matched duplex. On the other hand, if a mismatch lies outside of the region complementary to a MGB-oligonucleotide conjugate, discriminatory ability for unconjugated and MGB-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of MGB-oligonucleotides conjugates in this context lies in the fact that much shorter oligonucleotides compared to those used in the prior art (i.e., 20-mers or shorter), having greater discriminatory powers, can be used, due to the pronounced stabilizing effect of MGB conjugation.

In one group of embodiments, the MGB is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepines.

Further preferred minor groove binders are those selected from the formulae:

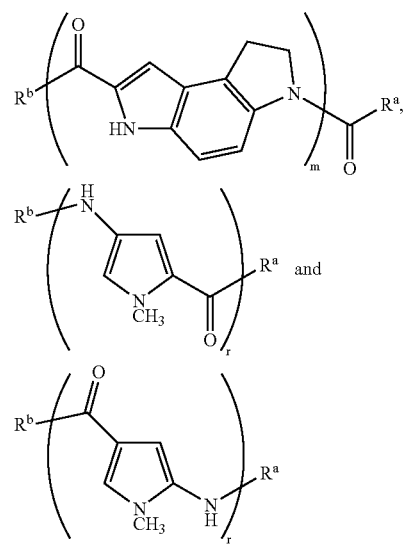

the subscript m is an integer of from 2 to 5; the subscript r is an integer of from 2 to 10; and each $R^a$ and $R^b$ is independently a linking group to the oligonucleotide (either directly or indirectly through a quencher), H, —OR$^c$, —NR$^c$R$^d$, —COOR$^c$ or —CONR$^c$R$^d$, wherein each R$^c$ and R$^d$ is selected from H, ($C_1$–$C_{12}$)heteroalkyl, ($C_2$–$C_{12}$)heteroalkenyl, ($C_2$–$C_{12}$)heteroalkynyl, ($C_1$–$C_{12}$)alkyl, ($C_2$–$C_{12}$)alkenyl, $(C_2-C_{12})$alkynyl, aryl$(C_1-C_{12})$alkyl and aryl, with the proviso that one of $R^a$ and $R^b$ represents a linking group to ODN or Q.

Particularly preferred minor groove binders include the trimer of 3-carbamoyl-1,2-dihydro-(3H)-pyrrolo[3,2-e]indole-7-carboxylate ($CDPI_3$), the pentamer of N-methylpyrrole-4-carbox-2-amide ($MPC_5$) and other minor groove binders that exhibit increased mismatch discrimination. Additional MGB moieties that will find use in the practice of the present invention are disclosed in co-owned U.S. Pat. No. 5,801,155. In certain embodiments, the MGBs can have attached water solubility-enhancing groups (e.g., sugars, amino acids, carboxylic acid or sulfonic acid substituents, and the like). See co-pending application Ser. No. 60/363, 602, filed Mar. 11, 2002.

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_0$) is described as the distance between the donor and acceptor molecules where the energy transfer is 50% efficient. Other mechanisms of fluorescence quenching are also known, such as, collisional and charge transfer quenching. There is extensive guidance in the art for selecting quencher and fluorophore pairs and their attachment to oligonucleotides (Haugland, R. P., HANDBOOK OF FLUORESCENT PROBES AND RESEARCH CHEMICALS, Sixth Edition, Molecular Probes, Eugene, Oreg., 1996; U.S. Pat. Nos. 3,996,345 and 4,351,760 and the like). Preferred quenchers are described in co-owned U.S. Ser. No. 09/457,616 (filed Dec. 8, 1999), and incorporated herein by reference. More particularly, Table 1 below contains structures of quenchers that can be readily modified to structures having suitable finctional groups (e.g., Q—W with attachment sites for ODN and MGB portions) for introduction into probes, based on the known chemical reactions cited (see, for example, Thiel, et al., *J. fur prakt. Chemie*, 328:497–514 (1986); U.S. Pat. Nos. 4,324,721 and 4,054,560; Timm, *Melliand Textilberichte*, 9:1090–1096 (1969); Hallas, *J.S.D.C.* 285–294 (1979); Beyer, et al., *J Prakt. Chem.*, 24:100–104 (1964); Hutchings, et al., *Chem. Europ. J.* 3:1719–1727 (1997) and Morley, et al., *J. Phys. Chem. A.*, 102:5802–5808 (1998); Haak, et al., *J. Chem. Res. Miniprint* 10:2701–2735 (1998) and Ruggli et al., *Helv. Chim. Acta*, 26:814–826 (1943). Additional structures (e.g., mono- and bis-azo dyes) with different combinations of substituents at various positions can be prepared based on compounds and methods known in the dye chemistry field (summarized in the Color Index, Issue 3 on CDD-ROM, pages 4009–4324; Society of Dyers and Colourists, Bradford, England; http://www.sdc.org.uk; and see also WO 01/86001).

TABLE 1

| Structure Literature | $\lambda_{max}$ $nM^{-1}$ $cm^{-1}$; Solvent | Linker-Modified Structure Q—W |
|---|---|---|
| [structure] | 464 | [structure] |
| [structure] | 440 | [structure] |
| [structure] | 540; 40,000 MeOH | [structure] |

TABLE 1-continued

| Structure Literature | λ_max nM$^{-1}$ cm$^{-1}$; Solvent | Linker-Modified Structure Q—W |
|---|---|---|
| (structure) | 549 37,000 EtOH | (structure) |
| (structure) | 590 48,978 CHCl$_3$ | (structure) |
| (structure) | 601 40,738 CHCl$_3$ | (structure) |
| (structure) | 623 48,000 CHCl$_3$ | (structure) |
| (structure) | 656 100,000 CHCl$_3$ | (structure) |
| (structure) | 656 53,043 | (structure) |
| (structure) | 598 | (structure) |

TABLE 1-continued

| Structure Literature | λ_max nM$^{-1}$ cm$^{-1}$; Solvent | Linker-Modified Structure Q—W |
|---|---|---|
| | 582 | |
| | 652 | |
| | 554 50,000 | |
| | 673.5 | |
| | 809 | |
| | 592 46,000 | |
| | 601 51,000 | |

TABLE 1-continued

| Structure Literature | $\lambda_{max}$ nM$^{-1}$ cm$^{-1}$; Solvent | Linker-Modified Structure Q—W |
|---|---|---|
| [structure: 2,6-dicyano-4-nitrophenyl azo 3-methoxy-4-(N,N-diethylamino)phenyl] | 623 48,000 | [structure: same core with —N(CH$_2$CH$_2$OH)$_2$ linker] |
| [structure: 2,6-dicyano-4-nitrophenyl azo 2-methoxy-5-methoxy-4-(N,N-diethylamino)phenyl] | 632 Predicted | [structure: same core with —N(CH$_2$CH$_2$OH)$_2$ linker] |

The quenchers above cover the range from about 400–800 nm, and many demonstrate improved quenching when attached to a MGB. While the modified versions illustrate —N(CH$_2$CH$_2$OH)$_2$ as a preferred linking group to be used to couple the quencher to oligonucleotides, MGB or solid support, examples of other suitable linkers are known in the art or are provided herein.

Preferred quenchers for each of the aspects of the invention herein are selected from those in the table above, as well as bis azo quenchers from Biosearch Technologies, Inc. (provided as Black Hole™ Quenchers: BH-1, BH-2 and BH-3), Dabcyl, TAMRA and carboxytetramethyl rhodamine.

Fluorophores

Fluorophores useful in the present invention are generally fluorescent organic dyes that have been derivatized for attachment to the terminal 5' carbon of the oligonucleotide probe, preferably via a linking group. One of skill in the art will appreciate that suitable fluorophores are selected in combination with a quencher which is typically also an organic dye, which may or may not be fluorescent.

There is a great deal of practical guidance available in the literature for selecting appropriate fluorophore-quencher pairs for particular probes. See, for example, Clegg (cited above); Wu et al. (cited above); Pesce et al., editors, FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic (quenching) molecules and their relevant optical properties for choosing fluorophore-quencher pairs, e.g., Berlman, HANDBOOK OF FLUORESCENCE SPECTRA OF AROMATIC MOLECULES, 2ND EDITION (Academic Press, New York, 1971); Griffiths, COLOUR AND CONSTITUTION OF ORGANIC MOLECULES (Academic Press, New York, 1976); Bishop, editor, INDICATORS (Pergamon Press, Oxford, 1972); Haugland, HANDBOOK OF FLUORESCENT PROBES AND RESEARCH CHEMICALS (Molecular Probes, Eugene, 1992); Pringsheim, FLUORESCENCE AND PHOSPHORESCENCE (Interscience Publishers, New York, 1949); and the like. Additionlly, methods for derivatizing fluorophores and quenchers for covalent attachment via common reactive groups are also well known. See, for example, Haugland (cited above); Ullman et al., U.S. Pat. No. 3,996,345; Khanna et al., U.S. Pat. No. 4,351,760; and the like.

Preferred fluorophores are those based on xanthene dyes, a variety of which are available commercially with substituents useful for attachment of either a linking group or for direct attachment to an oligonucleotide. Another group of fluorescent compounds are the naphthylamines, having an amino group in the α- or β-position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like. Still other suitable fluorophores include the resorufm dyes, rhodamine dyes, cyanine dyes and BODIPY dyes.

These dyes and appropriate linking methodologies for attachment to oligonucleotides are described in many references, e.g., Khanna et al. (cited above); Marshall, Histochemical J., 7:299–303 (1975); Menchen et al., U.S. Pat. No. 5,188,934; Menchen et al., European Patent Application 87310256.0; and Bergot et al., International Application PCT/US90/05565.

More particularly, the fluorophores described herein can be attached to the oligonucleotide portions using, for example, chemical or enzymatic methods. By way of example, methods for incorporation of reactive chemical groups into oligonucleotides, at specific sites, are well-known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. Nos. 5,824,796; 5,210,015; Kessler (ed.), Nonradioactive Labeling and Detection of Biomolecules, Springer-Verlag, Berlin, 1992; Kricka (ed.) Nonisotopic DNA Probe Techniques, Academic Press, San Diego, 1992; Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774–1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767. Examples of modifying enzymes include, but are not limited to, DNA polymerases, reverse transcriptases, RNA polymerases, etc. Examples of enzymes which are able to add a label to an already-existing oligonucleotide include, but are not limited to, kinases, terminal transferases, ligases, glycosylases, etc.

For each of the aspects of the present invention, preferred fluorophores are selected from cyanines, BODIPY analogs, 5-FAM™, 6-FAM™, TET™, JOE™, HEX™, VIC™, NED™, TAMRA™, ROX™, Bothell Blue™ and Yakima Yellow™ (YY). These fluorophores are generally available from commercial sources such as Applied Biosystems Inc., Foster City, Calif. and Epoch Biosciences, Inc., Bothell, Wash.

Linking Groups

A variety of linking groups and methods are known to those of skill in the art for attaching fluorophores, quenchers and minor groove binders to the 5' or 3' termini of oligonucleotides. See, for example, Eckstein, editor, OLIGONUCLEOTIDES AND ANALOGUES: A PRACTICAL APPROACH (IRL Press, Oxford, 1991); Zuckerman et al., *Nucleic Acids Research*, 15:5305–5321 (1987); Sharma et al., *Nucleic Acids Research*, 19:3019 (1991); Giusti et al., *PCR Methods and Applications*, 2:223–227 (1993), Fung et al., U.S. Pat. No. 4,757,141; Stabinsky, U.S. Pat. No. 4,739,044; Agrawal et al., *Tetrahedron Letters*, 31:1543–1546 (1990); Sproat et al., *Nucleic Acids Research*, 15:4837 (1987); Nelson et al., *Nucleic Acids Research*, 17:7187–7194 (1989); and the like. Still other commercially available linking groups can be used that can be attached to an oligonucleotide during synthesis, e.g., available from Clontech Laboratories (Palo Alto, Calif.). Other methodologies for attaching a fluorophore to an oligonucleotide portion involve the use of phosphoramidite chemistry at the conclusion of solid phase synthesis by way of dyes derivatized with a phosphoramidite moiety. See, for example, Woo et al., U.S. Pat. No. 5,231,191; Hobbs, Jr., U.S. Pat. No. 4,997,928; Reed, et al., PCT publication No. WO 01/42505; U.S. Ser. Nos. 09/876,830; 10/084,818; and 10/026,374.

While a number of general linking methods are available, the selection of certain linking groups constitute one aspect of the invention, when selection is made in combination with other factors such as oligonucleotide length, minor groove binders, fluorophore-quencher pairs, and the like. For example, in the present invention, the use of minor groove binders allows the preparation of probes having fewer nucleotide bases. In general, probes having fewer than about 15 bases have been considered unusable due to poor signaling and/or hybridization to target polynucleotides. Additionally, smaller probes (e.g., those of 15 or fewer bases) have been avoided for beacon assays as the quencher/fluorophore often are not sufficiently separated to provide a suitable signal upon hybridization.

In the present invention, shorter probes having attached minor groove binders are found to be useful, and sufficient spacing between the fluorophore and quencher can be obtained by selection of an appropriate linking group. Accordingly, the present invention provides novel probe/conjugates that are both efficient, inexpensive and useful in real-time assays.

The probes and conjugates of the present invention will generally have one or two types of linking groups. As provided in formula I, the letter K represents a divalent linking group, while the letter W represents a trivalent linking group. The particular linking groups are generally selected for their ease of synthesis, utility in solid phase synthesis, stability during probe construction and use, and the physical parameters each imparts to the probe or conjugate such as providing adequate separation between the fluorophore and the quencher; or providing a tether of suitable length to allow the minor groove binder portion to non-covalently interact with the minor groove formed upon probe hybridization.

More particularly, K is a direct bond between a fluorophore and the oligonucleotide portion of the probe/conjugate, or is a divalent linking group having from 1 to 30 main chain atoms that are selected from C, O, N, S, P and Si. Selection of a suitable linking group is generally made with consideration of the ODN length of the probe. Typically, shorter linking groups can be used when the ODN is longer than about 15–18 nucleotides, while longer linking groups are more useful when shorter probes are desired and/or constructed. In one group of preferred embodiments, K is a linking group having a formula selected from —(O—(CH$_2$)$_p$)$_q$— wherein the subscript p is an integer of from 2 to 14 and the subscript q is an integer of from 1 to 10, with the proviso that the overall length of K is less than about 50 atoms. Preferably, K is selected from —(OCH$_2$CH$_2$)$_3$—, —(OCH$_2$CH$_2$)$_6$—, —(O(CH$_2$)$_{12}$)— and —(O(CH$_2$)$_{12}$)$_2$—. In another group of embodiments, K is preferably a linking group having the formula:

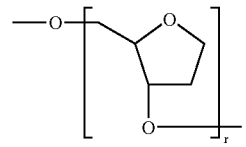

wherein the subscript r is an integer of from 1 to 5, preferably 1 or 2, most preferably 2.

The trivalent linking group W can encompass a variety of structures in order to provide suitable attachment and flexibility between the ODN, Q and MGB. In one group of embodiments, W is a trivalent functionality having the formula:

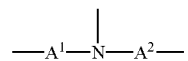

wherein the nitrogen atom is directly attached to an aromatic ring of a mono azo- or bis azo-dye (quencher, Q) and typically considered as part of the quencher, and the components A$^1$ and A$^2$ are independently selected from a bond or a linking/spacer portion having from 1 to about 50 atoms selected from C, N, S, P, Si and O, and additional hydrogen atoms to fill the available valences. Additionally, each of $A^1$ and $A^2$ can have cyclic components, acyclic (linear or branched) components, or a combination thereof.

Methods of Use

The probes/conjugates of the present invention provide numerous advantages over existing probes and conjugates, including superior mismatch discrimination. The probes/conjugates of the invention are particularly useful wherein their hybridization to a target sequence is detected in real-time (or coincident) with an amplification process such as, for example, PCR. Additionally, the probes/conjugates of the present invention are not digested by 5'-nuclease activity. Accordingly, the amplification reactions can be archived and reevaluated by melting curve analysis.

The probes/conjugates of the present invention are useful in other techniques in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; and techniques in which two or more oligonucleotides are hybridized to a target nucleic acid and interactions between the multiple oligonucleotides are measured. Conditions for hybridization of oligonucleotides, and factors which influence the degree and specificity of hybridization, such as temperature, ionic strength and solvent composition, are well-known to those of skill in the art. See, for example, Sambrook et al., supra; Ausubel, et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al. (1991) *Nucleic Acids Res.* 19:5143–5151. In still other methods, multiple probes can be used to detect alternate target site regions (e.g., th identify difficult sequences or to differentiate species and subspecies of the target).

Hybridization of probes and/or primers to target sequences proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are noncomplementary, or mismatched. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

For those probes/conjugates which incorporate modified bases, it is understood that the modified bases will retain the base-pairing specificity of their naturally-occurring analogues. For example, PPPG analogues are complementary to cytosine, while PPPA analogues are complementary to thymine and uracil. The PPPG and PPPA analogues not only have a reduced tendency for so-called "wobble" pairing with non-complementary bases, compared to guanine and adenine, but the 3-substituted groups increase binding affinity in duplexes. Similarly, modified pyrimidines hybridize specifically to their naturally occurring counter partners.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, concentration of organic solvents such as formamide and dimethylsulfoxide and chaotropes.

Thus, in the formation of hybrids (duplexes) between a probe/conjugate and its target sequence, the probe/conjugate is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, is determined by methods that are well-known in the art. A preferred method is to determine the $T_m$ of the hybrid duplex. This is accomplished, as described supra, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$s are known, a hybridization temperature (at fixed ionic strength, pH and solvent concentration) can be chosen that it is below the $T_m$ of the desired duplex and above the $T_m$ of an undesired duplex. In this case, determination of the degree of hybridization is accomplished simply by testing for the presence of hybridized probe.

In some embodiments, the probe/conjugate is capable of acting as a primer, and the degree of hybridization of the probe/conjugate can also be determined by measuring the levels of the extension product of the primer. In this embodiment, either the primer can be labeled, or one or more of the precursors for polymerization (normally nucleoside triphosphates) can be labeled. Extension product can be detected, for example, by size (e.g., gel electrophoresis), affinity methods with hybridization probes as in real time PCR, or any other technique known to those of skill in the art.

Primer extension ("minisequencing", "genetic bit analysis") assays are commonly used for SNP typing and have can also be used in other genotyping and mutation screening applications (Pastinen T. et al., *Genome Res.*, 10:1031–42 (2000)). In the present invention, the presence of minor groove binders and, in some cases, modified bases can improve primer extension assays. For example, the added duplex stability provided by MGB, or 5-substituted pyrimidine or 3-substituted pyrazolo[3,4-d]pyrimidine enables extensions to be performed at elevated temperatures. This is advantageous as problematic secondary structures in target molecules can be eliminated at elevated temperatures. Also, hybridization of target to primer is faster at higher temperature. Thermostable polymerases such as Taq polymerase and Bst DNA polymerase can be used in such reactions. While MGBs and modified bases can provide probes and primers have the advantages noted above, the use of a modified base will typically be in a position other than the 3'-terminal position in order to avoid primer extension inhibition.

Furthermore, MGBs and modified bases improve the specificity of assays by eliminating one class of false positive signals. Primer sequences that form hairpin structures or homodimers are prone to template-independent extension (the 5' end of the primer functions as template), resulting in false positive signal. MGBs and modified bases on "templates" inhibit extension by DNA polymerases. Thus, MGBs on the 5' end, or modified bases on the 5' end or middle of a primer, can prevent extension (false positives) from primer hairpins or primer dimers. Finally, PPG can be used to eliminate non-canonical structures formed by G-rich oligonucleotides, enabling primer extension assays in such sequences.

Other assays in which the present modified oligonucleotides are particularly useful are described in U.S. Pat. No. 6,312,894.

Still other amplification assays in which the present probes/conjugates are useful include the amplification assays based on the invasive cleavage of oligonucleotide probes by flap endonucleases (Lyamichev et al., *Nature Biotechnol.*, 17:292–296 (1999)); self-sustained sequence replication type assays (Mueller et al, *Histochem. Cell Biol.*, 108:431–437 (1997)) and the like. Surprisingly, non-natural bases can be substituted in both the invader and genomic probes of a cleavage-based assay. These modifications include but are not limited to pyrazolo[3,4-d]pyrimidines, 3-substituted pyrazolo[3,4-d]pyrimidines and 5-substituted pyrimidines. Non-natural backbones are also included such as monomers used in peptide nucleic acids, locked nucleic acids, and the like.

In view of the above, the present invention provides a method for continuous monitoring of polynucleotide amplification, comprising:

(a) combining a sample containing a target sequence, with one or more oligonucleotide primers complementary to regions of the target sequence, a polymerizing enzyme, nucleotide substrates, and an oligonucleotide conjugate having a formula:

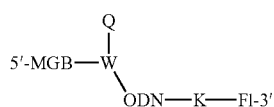

wherein MGB is a minor groove binder, Q is a quencher, W is a trivalent linking group, ODN is an oligonucleotide or modified oligonucleotide, K is a bond or a linking group and Fl is a fluorophore, and the ODN portion has a sequence complementary to a portion of the target sequence being amplified, to provide a mixture;

(b) incubating the mixture under conditions favorable for polymerization; and (c) continuously monitoring the amplification by monitoring the fluorescence produced upon conjugate hybridization to the amplified target.

Amplification procedures are those in which many copies of a target nucleic acid sequence are generated, usually in an exponential fashion, by sequential polymerization and/or ligation reactions. In addition to the more traditional amplification reactions discussed below, the present invention is useful in amplifications involving three-way junctures (see, WO 99/37085), signal amplification (see Capaldi, et al., *Nuc. Acids Res.*, 28:E21 (2000)), T7 polymerases, reverse transcriptase, RNase H, RT-PCR, Rolling Circles, cleavase and the like.

Many amplification reactions, such as PCR, utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases, etc. Conditions favorable for polymerization by different polymerizing enzymes are well-known to those of skill in the art. See, for example, Sambrook et al., supra; Ausubel, et al., supra; Innis et al., supra. Generally, in order to be extendible by a polymerizing enzyme, a primer must have an unblocked 3'-end, preferably a free 3' hydroxyl group. The product of an amplification reaction is an extended primer, wherein the primer has been extended by a polymerizing enzyme.

Thus, in one preferred embodiment of the invention, the methods and compositions disclosed and claimed herein are useful in improving and monitoring amplification reactions such as PCR. See, e.g., U.S. Pat. Nos. 4,683,202; 4,683,195 and 4,800,159; Mullis and Faloona, supra; and Saiki et al., supra. The polymerization step of PCR is most often catalyzed by a thermostable polymerizing enzyme, such as a DNA polymerase isolated from a thermophilic bacterium, because of the elevated temperatures required for the denaturation step of PCR. As discussed supra, one of the problems heretofore associated with the practice of PCR is the requirement for relatively long oligonucleotide primers, having sufficient hybrid stability to serve as primers at the elevated temperatures under which PCR is conducted. The probes/conjugates of the present invention are particularly useful as MGBs increase hybrid stability, thereby significantly extending the lower limit of useful probe length. In addition, MGB-modified oligonucleotide conjugates are useful in specialized PCR protocols wherein further reduced probe length is desirable. These include, but are not limited to, differential display, in which optimal primer or probe length is below 10 nucleotides, random amplification of polymorphism in DNA (RAPD) techniques, and amplification length polymorphism analyses. Liang et al, supra; Williams et al., supra.

The probes and primers described herein are applicable to any type of assay or procedure in which PCR or a related amplification technique is used, including, but not limited to, priming with allele-specific oligonucleotides (ASOs), fragment length polymorphism analysis, single nucleotide polymorphism (SNP) analysis and microsatellite analysis, for example. These and other techniques are useful in gene mapping, in the identification and screening of disease-related genes, and in pharmacogenetics, to name just a few applications.

In a related aspect, the present invention provides a method for monitoring gene expression comprising:
(a) providing an array of oligonucleotide probes of different sequences,
(b) incubating at least one population of polynucleotides with the array under hybridization conditions, and
(c) determining to which of the oligonucleotide probes in the array the population hybridizes;
wherein one or more of the oligonucleotide probes has the formula:

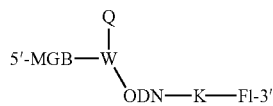

wherein MGB is a minor groove binder, Q is a quencher, W is a trivalent linking group, ODN is an oligonucleotide or modified oligonucleotide, K is a bond or a linking group and Fl is a fluorophore.

In one group of embodiments, the method is carried out with a plurality of expressed genes from multiple cell-types or tissues. Generally, the number of polynucleotide populations is from 1 to about 10, more preferably, from 1 to about 5, and still more preferably, 1, 2, 3 or 4 polynucleotide populations.

In these procedures, an ordered array comprising a plurality of probes/conjugates of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. See, for example, U.S. Pat. Nos. 5,492,806; 5,525,464; 5,556,752; and PCT Publications WO 92/10588 and WO 96/17957.

Materials for construction of arrays include, but are not limited to, nitrocellulose, glass, silicon wafers, polymeric materials, optical fibers and other materials suitable for construction of arrays such as are known to those of skill in the art.

In one group of embodiments, the probes of the present invention are immobilized on the solid support using conventional immobilization techniques with suitable spacers between the support and the probe for the hybridization interactions (including MGB binding in the minor groove of the hybrid) to proceed unencumbered by the support. In other embodiments, the probes of the present invention are used in a sandwich assay format.

One problem with current array-based sequencing and analysis methods is that the different oligonucleotides in an array will each have a different $T_m$. Hence, it is difficult to determine the stringency conditions that will provide maximum sensitivity, while retaining the ability to distinguish single-base mismatches. This is a particularly important consideration for most, if not all, applications of array technology. Use of probes and conjugates according to the present invention for array-based sequencing and analysis techniques provides a solution to this problem. Surprisingly, an MGB moiety in a modified oligonucleotide makes its $T_m$ relatively independent of base composition. Thus, for a population of modified oligonucleotides and MGB-modified oligonucleotide conjugates of a given length, the $T_m$ for a perfect hybrid falls within a relatively narrow temperature range regardless of sequence. At the same time, the $T_m$ for a single nucleotide mismatch is well below the $T_m$ of the perfect match. Thus, arrays designed such that all oligonucleotides contain some modified bases, are the same length, and are present as their MGB conjugates exhibit minimal variation in $T_m$ among the different oligonucleotides in the array, enabling more uniform hybridization conditions for the entire array. A further advantage to the use of modified oligonucleotides and MGB-modified oligonucleotide conjugates in these techniques is that it provides greater sensitivity, by allowing the use of shorter oligonucleotides, at higher temperatures (and hence higher stringency), while retaining single-nucleotide resolution.

An additional application of the present invention to array technology is in the examination of patterns of gene expression in a particular cell or tissue (see, generally, Eisen, et al., METHODS IN ENZYMOLOGY, 303:179–205 (1999)). In this case, the probes/conjugates of the present invention are arrayed on a surface, and a nucleic acid sample from a particular cell or tissue type, for example, is incubated with the array under hybridization conditions. Detection of the sites on the array at which hybridization occurs allows one to determine which probes have hybridized, and hence which genes are active in the particular cell or tissue from which the sample was derived.

Array methods can also be used for identification of mutations or polymorphisms, where wild-type and mutant sequences are placed in an ordered array on a surface (see, Hacia, et al., *J. Mol. Genet.*, 36:730–736 (1999)). Hybridization of a polynucleotide sample to the array under stringent conditions, and determination of which oligonucleotides in the array hybridize to the polynucleotide, allows determination of whether the polynucleotide possesses the wild-type or the mutant sequence. The increased discriminatory abilities of the probes and conjugates described herein are especially useful in this application of array technology.

In still another aspect, the present invention provides a method for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising:
(a) contacting the mixture of polynucleotides with an oligonucleotide conjugate having the formula:

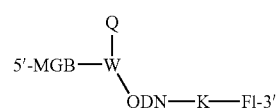

wherein MGB is a minor groove binder, Q is a quencher, W is a trivalent linking group, ODN is an oligonucleotide or modified oligonucleotide, K is a bond or a linking group and Fl is a fluorophore; and wherein the conjugate forms a stable hybrid only with said target sequence that is perfectly complementary to the ODN portion of said conjugate, and the conjugate does not form a stable hybrid with any of the other polynucleotides; and
(b) measuring the fluorescence produced on hybrid formation, whereby hybrid formation indicates the presence of said target sequence.

Preferably, at least one of the other polynucleotides has a target sequence with one or more base mismatches, more preferably only one base mismatch.

As noted above, a target sequence refers to a nucleotide sequence which comprises a site of hybridization for a probe or a primer. Target sequences can be found in any nucleic acid including, but not limited to, genomic DNA, cDNA, RNA and any amplified product thereof, and can comprise a wild-type gene sequence, a mutant gene sequence, a non-coding sequence, a regulatory sequence, etc. A target sequence will generally be less than 100 nucleotides, preferably less than 50 nucleotides, and most preferably, less than 21 nucleotides in length.

The conjugates used in this aspect of the invention are essentially the same as those that have been described herein and the polynucleotides can be distinguished by determining which polynucleotides hybridize to the oligonucleotide conjugate. Conditions for hybridization of oligonucleotide conjugates or probes are well-known to those of skill in the art. See, for example, Sambrook et al., supra; Ausubel et al., supra; Innis et al., supra; Hames et al. supra; and van Ness et al., supra.

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; etc. See, for example, Falkow et al., U.S. Pat. No. 4,358,535; Urdea et al., U.S. Pat. Nos. 4,868,105 and 5,124,246; Freifelder, *Physical Biochemistry*, Second Edition, W. H. Freeman & Co., San Francisco, 1982; Sambrook, et al., supra; Ausubel et al., supra; Hames et al., supra; and other related references. The duplex-stabilizing capability of the oligonucleotide conjugates described herein makes hybridization possible under more stringent conditions, wherein potentially occluding secondary structure in the target nucleic acid can be minimized. Accordingly, such oligonucleotide conjugates are particularly preferred in this aspect of the invention.

In one group of preferred embodiments, the oligonucleotide conjugate has at least one pyrazolo[3,4-d]pyrimidine and/or a 3-substituted pyrazolo[3,4-d]pyrimidine base. In this group of embodiments, the conjugate is hybridized to a target and/or an extension product of a target, and a change in the physical state of the fluorophore/quencher pair is effected as a consequence of hybridization.

The use of probes and conjugates of the present invention (5'-MGB-Q-ODN-Fl-3') in this and related methods allows greater speed, sensitivity and discriminatory power to be applied to these assays. In particular, the enhanced ability of the probes and conjugates to allow discrimination between a perfect hybrid and a hybrid containing a single-base mismatch will facilitate the use of real-time amplification assays in, for example, the identification of single-nucleotide polymorphisms and the like. One of skill in the art will appreciate that compositions and methods, such as those of the invention, that are capable of discriminating single-nucleotide mismatches will also be capable of discriminating between sequences that have 2, 3, 4, 5, or even 6 or more mismatches with respect to one another.

In yet another aspect, the present invention provides a method for distinguishing between wild-type, mutant and heterozygous target polynucleotides, the method comprising:
  (a) contacting a sample containing a target polynucleotide with two probes wherein a first probe is specific for the wild-type target polynucleotide and a second probe is specific for the mutant target polynucleotide, each of the probes having a formula:

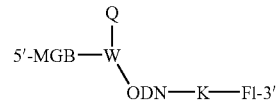

wherein MGB is a minor groove binder, Q is a quencher, W is a trivalent linking group, ODN is an oligonucleotide or modified oligonucleotide, K is a bond or a linking group and Fl is a fluorophore; wherein the first and second probes have different fluorophores and each of the probes forms a stable hybrid only with the target sequence that is perfectly complementary to the ODN portion of the probe; and
  (b) measuring the fluorescence produced on hybrid formation, whereby hybrid formation indicates the presence or absence of each of the wild-type, mutant and heterozygous target polynucleotides.

In this aspect of the invention the melting temperatures ($T_m$) for each hybrid produced between the first and second probes and their respective targets are preferably within about 5° C. of each other. In one group of preferred embodiments, the ODN portion of each of the probes is an oligonucleotide or modified oligonucleotide having from 8 to 18 bases or modified bases, more preferably, an oligonucleotide or modified oligonucleotide having from 10 to 15 bases or modified bases. In other preferred embodiments, the fluorophore portions of each of the probes are selected from cyanines, BODIPY analogs, 5-FAM™, 6-FAM™, TET™, JOE™, HEX™, VIC™, NED™, TAMRA™, ROX™, Bothell Blue™ and Yakima YelloW™ (YY). These fluorophores are available from Applied Biosystems Inc., Foster City, Calif. and from Epoch Biosciences, Inc., Bothell, Wash.

In still other preferred embodiments, the ODN portion of each of said probes contains at least one modified base. Preferably, each modified base is indenpendently selected from 6-amino-1H-pyrazolo[3,4-d]pyrimidin-4(5R)-one, 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-ynyl)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-ynyl)-1,3-dihydropyrimidine-2-one, 6-amino-5-(3-aminoprop-1-ynyl)-1,3-dihydropyrimidine-2-one, 5-[4-amino-3-(3-methoxyprop-1-ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine.

In other preferred embodiments, the sample is further contacted with a set of primers under amplification conditions and each of the primers contains from one to ten modified bases selected from the group provided above. Accordingly, in another aspect of the invention, kits are provided that contain probes/conjugates as described above, along with primers for amplification reactions, wherein the primers contain one or more modified bases, more preferably, from one to ten modified bases per primer.

EXAMPLES

Example 1

This example illustrates preparation and properties associated with the 5'-MGB-Q-ODN-Fl-3' probes of the present invention, particularly in comparison to related probes such as 3'-MGB-Q TaqMan® probes.

Materials and Methods 1.1 Templates

Human genomic DNAs from a pedigree family number 66 (homozygous for RRM1 (Human M1 Subunit of Ribonucleotide Reductase) allele 1 mother; homozygous for RRM1 allele 2 father and heterozygous son) were purchased from Coriell Institute of Medical Research, Camden, N.Y. Genotyping was previously done in our laboratory using restriction length polymorphism and TaqMan methods.

DNA fragment containing a partial sequence of glycoprotein D gene of Herpes Simplex Virus (HSV) type 1 was derived from DNA isolated from infected cells (Strain F from ATCC#VR-733) by PCR. PCR fragment was gel-purified and quantitated by UV absorption.

Human DNA samples were obtained (Coriell Institute of Medical Research, Camden, N.Y.) and typed for CYP2D6 and CYP2D6*4 alleles.

1.2 Oligonucleotides

Sequences of oligonucleotides used are shown in Table 2. Primers were synthesized using standard phosphoramidite chemistry. The 5'-MGB-Q Eclipse™ probes were prepared by automated DNA synthesis on a MGB-Q-modified glass support (manuscript in preparation) using 5'-β-cyanoethyl phosphoramidites (Glen Research, Va.) designed for synthesis of oligonucleotide segments in 5'→3' direction. Oligonucleotide synthesis was performed on an ABI 394 synthesizer according to the protocol supplied by the manufacturer using a 0.02M iodine solution. PPG phosphoramidites were synthesized based on literature methods, but can also be purchased from Glen Research, Sterling, Va. 6-Carboxyfluorescein (FAM), Yakima Yellow™ (YY, from Epoch Biosciences, Inc., Bothell, Wash.) and 6-carboxy-4,7,2',7'-tetrachlorofluorescein (TET) reporting dyes were introduced at the last step of the synthesis using the corresponding phosphoramidites (Glen Research, Sterling, Va.). The 3'-MGB-Q TaqMan® probe corresponding to RRM1 allele 1 SNP was synthesized as described for the preparation of the MGB Eclipse™ Probes. Standard 5'-DMT phosphoramidites were used in this instance. All oligonucleotides were purified by reverse phase HPLC.

TABLE 2

SEQUENCE OF PRIMERS AND FLUOROGENIC PROBES

|  | 5'-end | SEQUENCE | 3'-end | SEQ ID NO: |
|---|---|---|---|---|
| RRMI (120 bp amplicon) Accession number XM_006065 | | | | |
| Primer 1 (sense) |  | ATG GCC TTG TAC CGA TGC TGA |  | 8 |
| Primer 2 (antisense) |  | GTA CTT TCA ATT CAT GGA GCA TAC CT |  | 9 |
| Eclipse ™ probe allele 1 (sense) | MGB-Q | ATA TCT AGC TGT GTT GA** | FAM | 10 |
| Eclipse ™ probe allele 2 (sense) | MGB-Q | ATA TCG AGC TGT GTT GA | TET | 11 |
| MGB-TaqMan allele 1 (sense) | FAM | ATA TCT AGC TGT GTT G | MGB-Q | 12 |
| CYP2D6*4 (127 bp amplicon) Accession number M33388 | | | | |
| Primer 1 (sense) |  | TGA TGG GCA GAA GGG CAC AA |  | 13 |
| Primer 2 (antisense) |  | ATC ACG TTG CTC ACG GCT TTG TC |  | 14 |
| Eclipse ™ probe allele 1 (WT) | MGB-Q | CGT CCT GgG GgT G | FAM | 2 |
| Eclipse ™ probe allele 1 (mutant) | MGB-Q | GGC GTC TTG gGg GT | YY | 3 |
| Human herpes virus 1,2 (142 bp amplicon) Accession number AF333383 | | | | |
| Primer 1 (sense) |  | ATC CGA ACG CAG CCC CGC TG |  | 15 |
| Primer 2 (antisense) |  | TCT CCG TCC AGT CGT TTA TCT TC |  | 16 |
| Eclipse ™ probe (antisense) | MGB-Q | CCC AGG TTA TCC TCG CT | FAM | 17 | g is PPG.
**Italicized letters represent unpaired base introduced to avoid quenching of FAM fluorescence by guanine. Underlined bold letters represent SNPs.

1.3 $T_m$ Prediction

MGB Eclipse™ Design Software 1.0 (Epoch Biosciences, Bothell, Wash.) was used to design the 5'-MGB-Q-ODN-Fl probes. One of the features of the software is the ability to design probes containing more than three consecutive Gs, known to be poor detection probes due to G:G self-association, and indicating an appropriate substitution of G with PPG.

Additionally, the software can now design probes that incorporate Super A and Super T modified bases in AT-rich sequences to improve duplex stability. The TaqMan® probes were designed using Primer Express® (AB Biosystems, Foster City, Calif.).

1.4 Real Time PCR

Real time PCR was conducted in either an ABI Prism® 7700 (Applied Biosystems, Foster City, Calif.), RotorGene, (Phenix Research Products, Hayward, Calif.), or a Light Cycler LC 24 (Idaho Technology Inc., Salt Lake City, Utah) thermocycling fluorimeter.

On the ABI Prism 7700 instrument, 50 cycles of three step PCR (95° C. for 30 s, 56° C. for 30 s and 76° C. for 30 s) after 2 min at 50° C. and 2 min at 95° C. were performed. The reactions contained 0.25 µM MGB Eclipse™ probe, 100 nM primer complementary to the same strand as the probe, 1 µM opposite strand primer, 125 µM dATP, 125 µM dCTP, 125 µM TTP, 250 µM dUTP, 0.25 U JumpStart DNA polymerase (Sigma), 0.125U of AmpErase Uracil N-glycosylase (Applied Biosystems) in 1× PCR buffer (20 mM Tris-HCl pH 8.7, 40 mM NaCl, 5 mM $MgCl_2$) in a 10 µL reaction. AmpErase uracil N-glycosylase was used with dUTP (instead of TTP) in all PCR reactions. Amount of the added template is indicated in the Results section. The increase in fluorescent signal was recorded during the annealing step of the reaction.

For those experiments, performed in the Light Cycler, the PCR mixture was the same as above, with the exception that non-acetylated Bovine Serum Albumin was added to the final concentration of 250 µg/µl. Cycling was performed as follows: 2 min at 50° C., 2 min at 95° C., followed by 50 cycles of 0 s at 95° C., 20 s at 56° C. and 20 s at 76° C. or as indicated. Final concentration of fluorogenic probes (MGB Eclipse™ and MGB-TaqMan) was 0.25 µM. Primer concentrations for the MGB Eclipse™ probes were the same as for ABI 7700. Primer concentration for the MGB-TaqMan was 0.50 µM each. The increase in fluorescent signal was registered during the annealing step of the reaction or as indicated. The results were taken directly from the screen or transferred to Excel format as instructed by manufacturers.

For those experiments, performed in the RotorGene, conditions similar to those employer with the Light Cycler were used except that cycling was performed as follows: 2 min at 50° C., 2 min at 95° C., followed by 50 cycles of 1 s at 95° C., 10 s at 56° C. and 4 s at 76° C., or as otherwise indicated.

1.5 Dynamic Range of MGB Eclipse™ Probes

Among the advantages of real time PCR techniques are the wide dynamic range and high sensitivity. We have titrated numerous DNA fragments from viral and other sources to determine the sensitivity and dynamic range of the MGB Eclipse™ probes. Typically, a range of $5 \times 10^7$ to 5 copies per reaction is detected with excellent reproducibility. A representative amplification plot (FIG. 3) shows an HSV type 1 titration from $5 \times 10^6$ down to 5 copies. The threshold cycle ($C_t$) values for these reactions were from 16 to 37 respectively. When $C_t$ was plotted against the LogN (N is the number of input target copies), the resulting standard curve is linear over 7 orders of magnitude with a correlation coefficient of 0.999. Quantitative PCR analysis with MGB Eclipse™ probes provides a wide linear dynamic range of amplification, and sensitivity down to a few copies.

1.6 Design of CYP2D6*4 allele specific probe containing five guanines in a row.

The polymorphic cytochrome P450 2D6 (CYP2D6) responsible for ultrarapid metabolism of several clinically important drugs exhibits pronounced interethnic variation. The allele CYP2D6*4 is the most common defective gene prevalent in Caucasians. The G/A mismatch is flanked by 5 consecutive Gs on the 5'-end and 4 consecutive Cs on the 3'-end. Not surprisingly, initial attempts to design normal discriminator probes against both strands failed. It is well established that sequences with 4 or more repetitive Gs in a row should be avoided (Primer Express®, AB Biosystems, Foster City, Calif.). The MGB Eclipse™ Design Software considers sequences containing more than 3 Gs in a row and suggests appropriate PPG substitution in order to circumvent G:G self-association. A G-rich CYP2D6*4 target was chosen to demonstrate the efficiency of the probe and primer design.

The first step in the design of probe and primers with MGB Eclipse™ Design Software is to import the sequence of the target of interest. A portion of CYPD6*4 gene is shown below (SEQ ID NO:18) and is imported from Genebank Accession number M 33388.

3001 gggtcttccc tgagtgcaaa ggcggtcagg gtgggcagag acgaggtggg gcaaagcctg 3061 ccccagccaa gggagcaagg tggatgcaca aagagtgggc cctgtgacca gctggacaga 3121 gccagggact gcgggagacc aggggagca tagggttgga gtgggtggtg gatggtgggg 3181 ctaatgcctt catggccacg cgcacgtgcc cgtcccaccc ccaggggtgt tcctggcgcg 3241 ctatgggccc gcgtggcgcg agcagaggcg cttctccgtg tccacctgc gcaacttggg 3301 cctgggcaag aagtcgctgg agcagtgggt gaccgaggag gccgcctgcc tttgtgccgc 3361 cttcgccaac cactccggtg ggtgatgggc agaagggcac aaagcgggaa ctgggaaggc 3421 gggggacggg gaaggcgacc ccttacccgc atctcccacc ccca[g/a]gacgc cccttttcgcc 3481 ccaacggtct cttggacaaa gccgtgagca acgtgatcgc ctccctcacc tgcgggcgcc 3541 gcttcgagta cgacgaccct cgcttcctca ggctgctgga cctagctcag gagggactga 3601 aggaggagtc gggctttctg cgcgaggtgc ggagcgagag accgaggagt ctctgcaggg 3661 cgagctcccg agaggtgccg gggctggact ggggcctcgg aagagcagga tttgcataga 3721 tgggtttggg aaaggacatt ccaggagacc ccactgtaag aagggcctgg aggaggaggg 3781 gacatctcag acatggtcgt gggagaggtg tgcccgggtc aggggggcacc aggagaggcc 3841 aaggactctg tacctcctat ccacgtcaga gatttcgatt ttaggtttct cctctgggca A portion of the CYP2D6*4 gene sequence. The mismatch is indicated in brackets.

Figure 4:
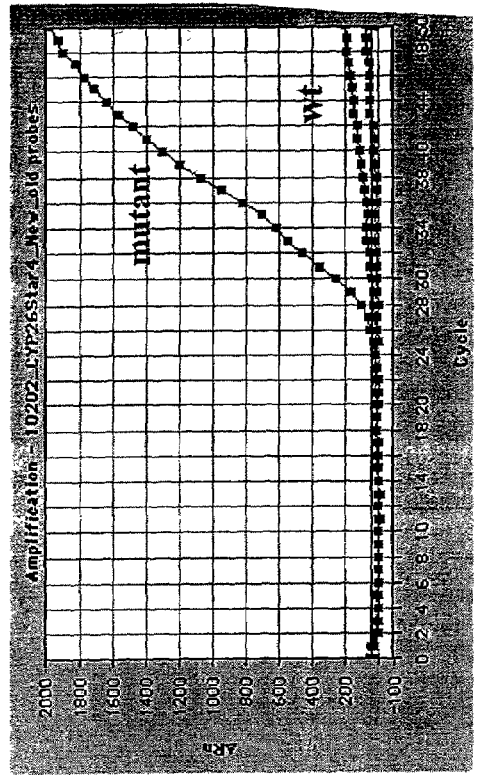
FIG. 4 illustrates a real time detection of a C/T polymorphism with super G containing probes in CYP2D6 gene. "C" probe (SEQ ID NO:2) is labeled with FAM; "T" probe (SEQ ID NO:3) is labeled with Yakima Yellow™. The left curve is a "TAM" channel with "C" DNA showing a positive curve and "T" DNA curve negative (staying flat). The right curve is a "Yakima Yellow" channel with "T" DNA curve positive and "C" DNA curve negative. Also negative is no template control in both channels.
Figure 4:
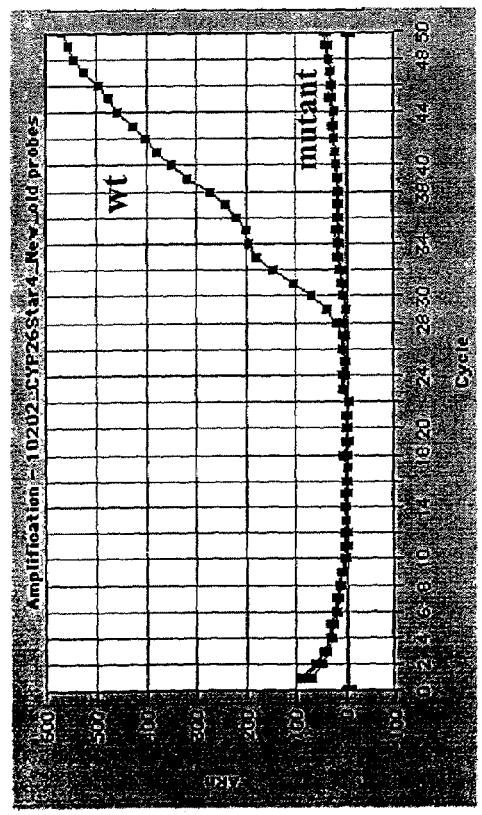

The software identifies a number of allele specific probes with their associated primers. Every probe, primer and amplicon is evaluated against a set of minimum and maximum parameter constraints. If the probe, primer or amplicon fails to satisfy a constraint, the evaluation process is halted. The probes and their primers are ranked based on a best fit of optimum parameter constraints (MGB Eclipse™ Design Software Manual, Epoch Bioscience, Bothell, Wash.). In Table 3, three sets of primers and probes, determined by the software, are listed. The listed order of the probes and primers are indicative of how close they are to ideal parameter constraints. The design of the three probe and primer sets were similar, the first design set was synthesized and used to differentiate between wild type and mutant as shown in FIG. 4.

TABLE 3

Probes and primers designed by MGB Eclipse™ Design Software. Where C and T indicate the mismatch and g=PPG

| ODN | $T_m$ | GC% | Length | Sequence | SEQ ID NO: |
|---|---|---|---|---|---|
| WT | 67.3 | 77 | 13 | CGTCCTGgGgGTG | 19 |
| Mutant | 67.8 | 71 | 14 | GGCGTGTTGgGgGT | 20 |
| Primer 1 | 68.6 | 55 | 20 | TGATGGGCAGAAGGGCACAA | 13 |
| Primer 2 | 67.9 | 52 | 23 | ATCACGTTGCTCACGGCTTTGTC | 14 |
| | | | | | |
| WT | 67.3 | 77 | 13 | CGTCCTGgGgTG | 21 |
| Mutant | 67.8 | 71 | 14 | GGCGTCTTGgGgGT | 20 |
| Primer 1 | 68.6 | 55 | 20 | TGATGGGCAGAAGGGCACAA | 13 |
| Primer 2 | 678 | 55 | 22 | TCACGTTGCTCACGGCTTTGTG | 22 |
| | | | | | |
| WT | 67.3 | 77 | 13 | CGTCCTGgGgGTG | 19 |
| Mutant | 67.8 | 71 | 14 | GGCGTGTTGgGgGT | 20 |
| Primer 1 | 68.7 | 52 | 21 | TGATGGGCAGAAGGGCACAAA | 23 |
| Primer 2 | 67.9 | 52 | 23 | ATCACGTTGCTCACGGCTTTGTC | 14 |

The two PPG containing probes specifically detect their corresponding targets. In contrast, probes containing all natural bases failed to detect their targets.

1.7 Allelic discrimination of CYP2D6 and CYP2D6*4 alelles

Figure 5:
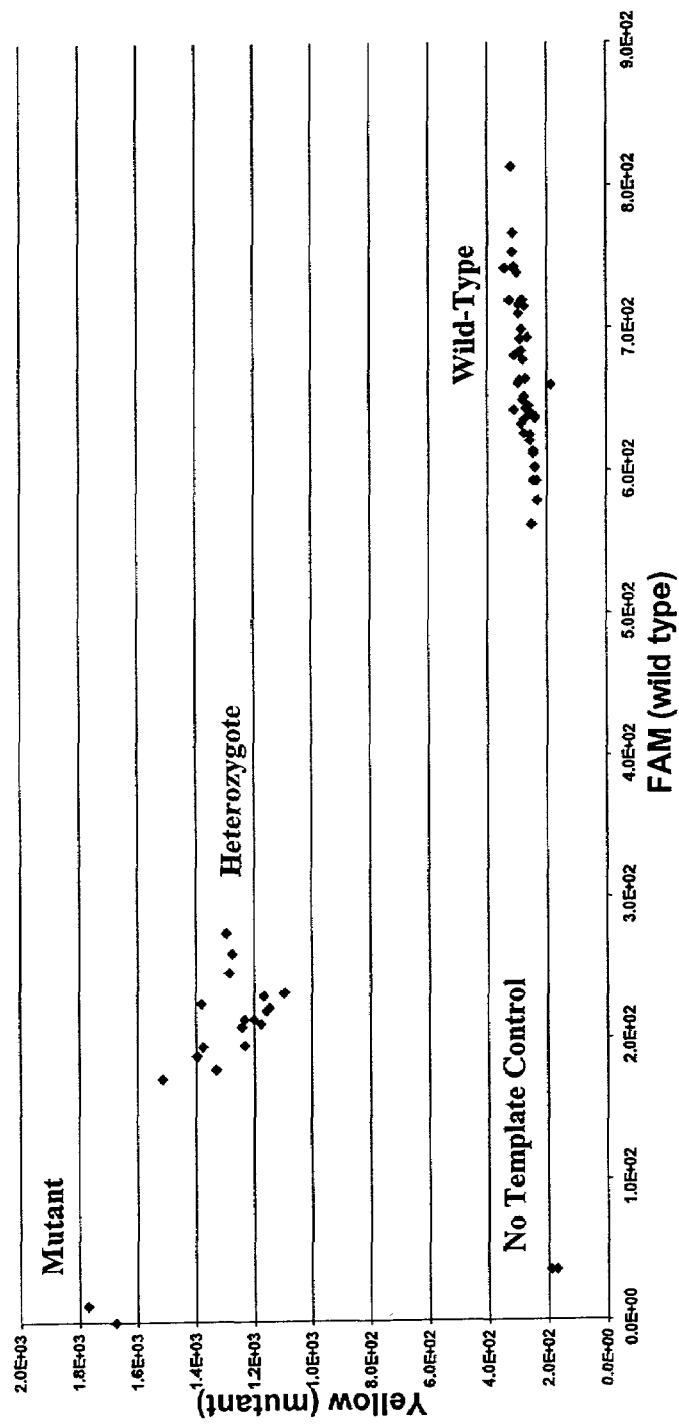
FIG. 5 is a Scatter diagram of real-time MGB-Eclipse™ probe detection of CYP2D6 alleles in DNA samples.

The designed probes for CYP2D6 alleles (Table 2) were used to evaluate their ability to genotype 34 CEPH DNA samples in duplicate (1 no template control, 26 wild-types, 7 heterozygotes and 1 mutant). Accurate genotyping is possible by MGB Eclipse™ probe assay as shown in FIG. 5. Fluorescence signal taken at the last amplification cycle, after background subtraction, for both channels were plotted. The scatter diagram (FIG. 5) demonstrates excellent clustering of homogygous, heterozygous and mutant samples 1.8 Design of Problematic Primers Some GC-rich primers are poor participants in amplification reactions. The poor performance of primers containing more than 4 consecutive Gs can also be eliminated by the appropriate substitutions of G by PPG. An example of a primer designed by the MGB Eclipse™ Design Software containing 4 consecutive Gs is shown for β-actin gene expression assay in Table 4, where one G is substituted by PPG. Successful amplification and detection were observed using the primers and detection probe listed in Table 4 (data not shown).

TABLE 4

Primers and probes for the detection of β-actin gene

Primer 1: GCG TGA TGG TGG GCA T sense
(SEQ ID NO:24)

Primer 2: GAT GgG GTA CTT GAG GGT antisense
(SEQ ID NO:25)

Probe: MGB-Q- GGA TTC CTA TGT GGG CGA -FAM sense
(SEQ ID NO:26)

1.9 Discussion

The 5'-MGB-Q-ODN-Fl (GB Eclipse™) probes of the present invention represent a sensitive alternative for real-time detection of amplified targets. The crescent shaped minor groove binder (FIG. 1) stabilizes AT-rich sequences preferentially, increasing $T_m$s of probes with as much as 20° C., allowing the use of short specific probes. This property is particularly advantages in probe design for single nucleotide polymorphism (SNP) detection and for short conserved sequences of viral genomes or multi-gene families. The new MGB Eclipse™ probes incorporate the beneficial futures of the MGB and Eclipse™ quencher technology. The probes in solution are efficiently quenched but fluoresce when hybridized to the amplified target (FIG. 1B). FIG. 2A demonstrates that the 5'-MGB-Q-ODN-Fl probes are not cleaved during amplification in contrast to that of a 3'-MGB-Q-ODN-Fl, TaqMan® probe (FIG. 2B). The intact 5'-MGB-Q-ODN-Fl probe provides a number of advantages over competitors. The MGB Eclipse™ probes can be used to detect targets in other non-5'-nuclease assays. In addition, duplexes could be melted post-amplification to determine the $T_m$ of viral types.

Figure 3:
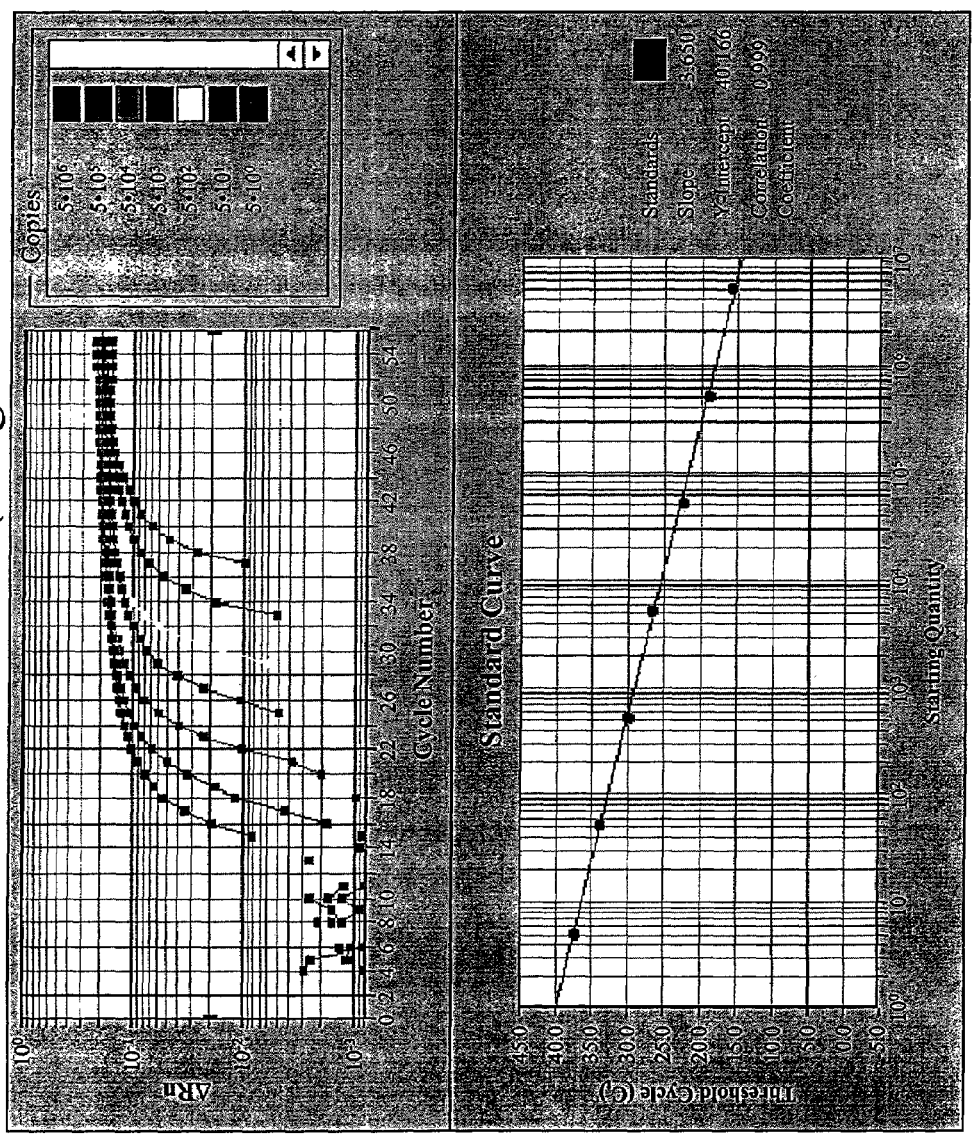
FIG. 3 illustrates demonstrates the sensitivity of MGB-Q-ODN-Fl probes. A titration of HSV DNA target (Range $5 \cdot 10^6 \rightarrow 5 \cdot 10^0$ Copies) illustrate an excellent dynamic range with single copy detection ability.

The high sensitivity and wide dynamic range of the MGB Eclipse™ probes is demonstrated in FIG. 3. The DNA fragments containing Herpes Simplex Virus (HSV) type 1 were titrated from $5 \times 10^6$ down to 5 copies. The $C_t$ (threshold cycle) values for these reactions were from 26 to 37 respectively. When $C_t$ was plotted versus the LogN of the number of input target copies, the resulting standard curve is linear for 7 orders of magnitude with correlation coefficient of 0.999.

The new MGB Eclipse™ Design Software not only allows the design of 5'-MGB-Q-oligonucleotides, but it also for the first time, enables the design of probe and primers for targets that contains more than 4 consecutive Gs. The use of more than 4 consecutive Gs in a row is not allowed in most software programs. The allele CYP2D6*4 is the most common defective gene prevalent in Caucasians and the G/A mismatch is flanked by 5 consecutive Gs on the 3'-end and 4 consecutive Gs on the 5'-end in the antisense-strand. Conventional probe design for this allele using both strands failed. However, using the MGB Eclipse™ Design Software three sets of primers and probes designed in this region, is shown in Table 3. All three probes contain 5 consecutive Gs and the software indicated PPG substitution for 2 of the 5 consecutive Gs. The first set of designed probes and primers were used in an amplification reaction and specifically detected the wild-type and the mutant CYP2D6*4 alleles (FIG. 4) confirming the ability of PPG substitution for G to eliminate G:G self-association. The ability of these MGB Eclipse™ probes to genotype 34 samples accurately for the different CYP2D6 alleles is shown in FIG. 5. The tight clustering confirms the utility of the MGB Eclipse™ probe system in SNP analysis.

Probes and primers for the sensitive MGB Eclipse™ probe detection system can now routinely be designed with the new MGB Eclipse™ Design Software. This software allows not only the design of 5'-MGB-Q-ODN-Fl (Eclipse™) probes, but for the first time allows the incorporation of PPG into the designed probes, when indicated. Probes and primers containing more than 4 consecutive Gs in a row, known to perform poorly, can now readily be designed to yield sensitive and specific probes. The use of PPG and MGB in the design of primers simplifies the design of primers with improved performance. The fact that the Eclipse™ probes are not cleaved during the amplification reactions makes them attractive as detection probes in other amplification systems.

Example 2

This example illustrates the real-time monitoring of amplification using three types of fluorogenic probes. A discussion of the results are provided above, with reference to FIG. 2.

To support the evidence of the probe degradation (or lack of it) during PCR, the fluorescent label was substituted with a radioactive one. As expected, MGB Eclipse™ probes showed no traces of degradation after the completion of PCR (FIG. 2, Aii). Molecular Beacon probe was more than 30% digested by Taq Polymerase (FIG. 2, Bii). TaqMan® MGB was almost completely digested (FIG. 2, Cii). None of the probes was heat-degraded during PCR (see no enzyme controls in FIG. 2, ii).

Radioactive Labeling of the Oligonucleotides

To monitor the digestion of TaqMan® MGB, Molecular Beacon and MGB Eclipse™ probes by Taq Polymerase during PCR, the corresponding oligonucleotides were labeled with $^{32}$P. The 5'-ends of TaqMan® MGB probe and Molecular Beacon were phosphorylated with T4 polynucleotide kinase (Promega, Madison, Wis., ISA) and [γ-$^{32}$P]ATP (5000 Ci/mmol, 10 mCi/ml, Amersham Pharmacia Biotech). The 3'-end of MGB Eclipse™ probe was labeled with terminal deoxynucleotidyl transferase (Promega, Madison, Wis., USA) and [α-$^{32}$P] cordycepin triphosphate (Perkin Elner Life Sciences Inc., USA).

PCR with Radioactive Probes

PCR conditions with radioactive probes were the same as for the real time PCR with the exception that the control reactions did not contain Taq polymerase. After completion of the PCR aliquots of each sample were separated on a denaturing polyacrilamide gel. Phosphor imaging was used to estimate degradation of the probes.

For the PCR in the Light Cycler, the PCR mixture was the same, with the exception that non-acetylated Bovine Serum Albumin was added to a final concentration of 250 μg/μl. Cycling was performed as follows: 2 min at 50° C., 1 min at 95° C., followed by 50 cycles of 0 s at 95° C., 20 s at 56° C. and 30 s at 76° C. Final concentration of fluorogenic probes (MGB Eclipse™, Molecular Beacon and TaqMan® MGB) was 250 nM. Primer concentrations for the MGB Eclipse™ probes were the same as for ABI 7700. Primer concentration for the Molecular Beacon and TaqMan® MGB was 0.50 μM each. Fluorescence was registered during annealing and denaturing steps of the reaction.

Results were taken directly from the screen or clipped files were transferred to Excel as instructed by the manufacturers.

Table 5 provides the sequence of primers and fluorogenic probes used in this example and illustrated in FIG. 2.

TABLE 5

Sequence of primers and fluorogenic probes

| | 5'-end | Sequence | 3'-end | SEQ ID NO: |
|---|---|---|---|---|
| | | RRM1 T1037G mutation; accession number XM 006065 | | |
| Primer 1 (sense) | | ATG GCC TTG TAC CGA TGC TGA | | 8 |
| Primer 2 (antisense) | | GTA CTT TCA ATT CAT GGA GCA TAC CT | | 9 |
| MGB Eclipse™ probe allele 1 (sense) | MGB-Q | ATA TC<u>T</u> AGC TGT GTT GA** | FAM | 10 |
| MGB Eclipse™ probe allele 2 (sense) | MGB-Q | ATA TC<u>G</u> AGC TGT GTT GA | TET | 11 |
| Molecular beacon allele 1 (sense) | FAM | cca acc AT CCA CAT ATC <u>T</u>AG CTG TGT TG ggt tgg* | Dabcyl | 27 |
| TaqMan® MGB allele 1 (sense) | FAM | ATA TC<u>T</u> AGC TGT GTT G | MGB-Q | 12 |

Example 3

This example illustrates the real time detection of c-myc gene expression using a 5'-MGB-Q-ODN-Fl-3' probe. Real time RT-PCR was done in two steps (reverse transcription and PCR in different tubes and reaction conditions) or in one step (RT and PCR combined).

Two-step RT PCR was performed using Clontech Advantage RT-for-PCR kit. Total RNA from human placenta and random primers were supplied by manufacture. 1 μL of a completed RT reaction was used as a template in 10 μL real-time PCR reactions with appropriate primers and FAM-labeled RTL probe as described above.

Figure 6:
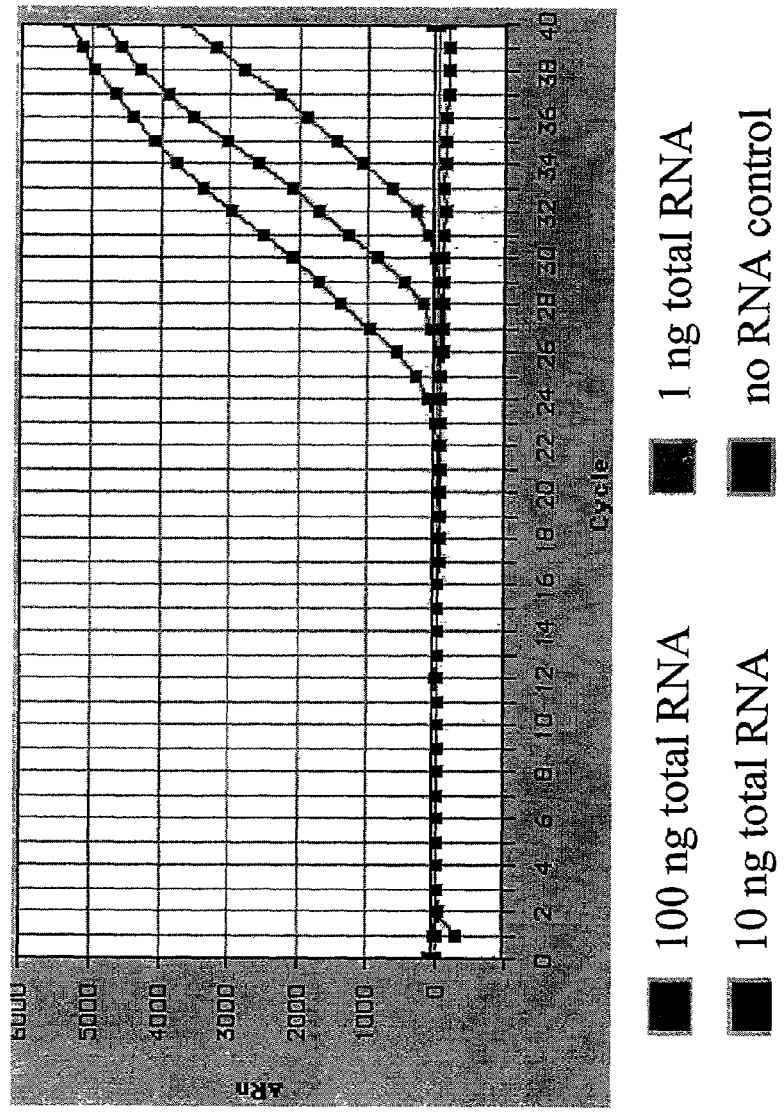
FIG. 6 illustrates the RT-PCR detection of c-myc gene expression.

One tube reaction was performed using QIAGEN One-Step RT-PCR Kit with different amounts of total RNA from human placenta (100 ng to 1 ng) per reaction. The protocol suggested by the manufacturer was followed with minor exceptions. Instead of recommended 0.6 μM of each gene-specific primer, 1 μM of antisense primer and 0.1 μM of a sense primer were used. MGB-Q-ODN-Fl probe (sense) was added to a final concentration of 0.2 μM to enable real time detection. RNase inhibitor was used at 5 units per reaction. Thermal cycler conditions were within recommended range and included 30 min at 50° C. for Reverse transcription, 15 min at 95° C. for initial PCR activation step, and 40 3-step cycles of denaturation (30 sec at 94° C.), annealing (30 sec at 56° C.), extension (30 sec at 76° C.). Extension time was reduced to 30 sec from 1 min due to small size of amplicons. Extension temperature was elevated from 72° C. to 76° C. to ensure that all MGB-Q-ODN-Fl probes are melted off the growing DNA strand and don't clamp PCR. The final extension step was omitted. Fluorescent readings were taken at annealing stage of PCR. FIG. 6 demonstrates the RT-PCR gene expression detection of a c-myc target.

Example 4

This example illustrates the determination of background fluorescence for probes used in the present invention.

Background fluorescence of FAM-labeled oligonucleotides with different quenchers was measured in triplicate at 0.2 μM concentration in 1X PCR buffer (20 mM Tris-HCl pH 8.7, 50 mM NaCl, 5 mM MgCl$_2$) using Applied Biosystems LS50-B Spectrophotometer. The excitation wavelength was 488 nm with the slit opening of 2.5. Emission wavelength was 522 nm with the slit opening of 5.5. Probes were prepared by an automated DNA synthesis with Eclipse™ Quencher (see co-pending application Ser. No. 09/457,6 16), Dabcyl, or MGB-Quencher. The probe sequence was 5'-tcctgattttac (SEQ ID NO:28).

Example 5

This example illustrates SNP detection of MTHFR gene by melting curve analysis.

Figure 7:
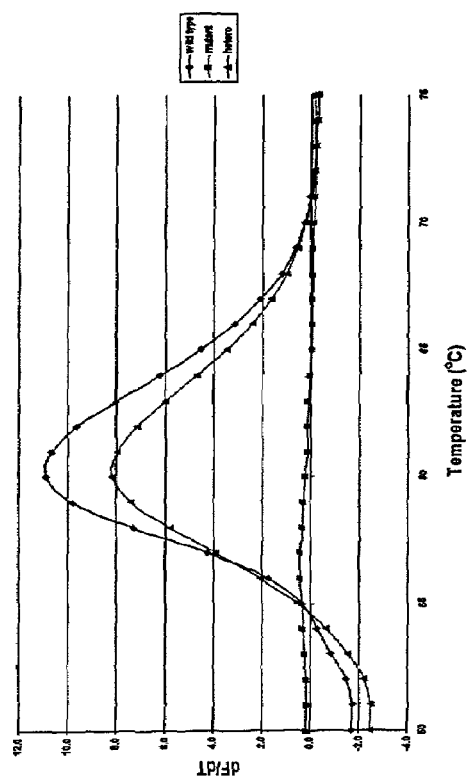
FIG. 7 illustrates the detection of wild-type, heterozygous and mutant MTHFR alleles by melting curve analysis. Each tube contains both probes (SEQ ID NOS:4 and 5) and 10 ng of human genomic DNA. Melting curves were obtained for each probe in the appropriate emission channel after PCR amplification.
Figure 7:
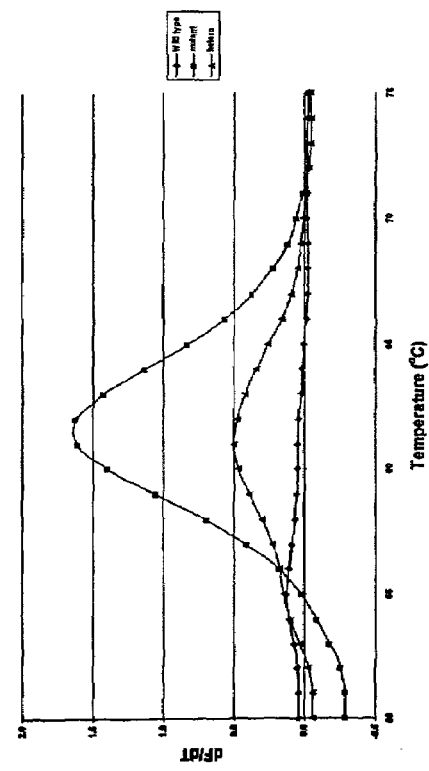

In this example, single base mismatch determination is made with a pair of probes of the invention. Amplification is performed with the probe for allele 1, labeled with fluorophore 1, and probe for allele 2, labeled with fluorophore 2 in the same tube. These probes are designed to have similar melting temperatures. PCR amplification is performed with probes for both alleles in each sample tube. When amplification is completed, the melting temperature ($T_m$) for each probe duplex is determined at two wavelengths, one for fluorophore 1 and one for fluorophore 2. If only homogeneous allele 1 target is present, a melt curve with only the fluorophore 1-labeled probe is obtained (FIG. 7A; melt curve in the FAM channel only). Similarly if only homogeneous allele 2 target is present, a melting curve with only fluorophore 2-labeled probe is obtained (FIG. 7B; melt curve only in the YY channel). However, in the case of a heterozygous target, melting curves are obtained with both the fluorophore 1- and fluorophore 2-labeled probes see FIGS. 7A and 7B (melt curves present in both channels). Instruments such as the RotorGene, Corbett Instruments, Australia, have the ability to compile different samples in one channel as shown in the Figure.

For the MTHFR gene, the probe sequence for the Wild Type allele is MGB-Q-ATC GGC TCC CGC-FAM (SEQ ID NO:4) and the probe sequence for the Mutant allele is MGB-Q-AAT CGA CTC CCG C-YY (Yakima Yellow™) (SEQ ID NO:5). The melting curves for wild type, mutant and heterozygous samples are compiled in FIG. 7A (FAM channel) and FIG. 7B (YY channel).

Example 6

This example illustrates utilization of modified bases in both primers and probes in SNP detection in an AT-rich region.

Below is shown an AT-rich sequence of interest (SEQ ID NO:29). Both primers and probes needed to be heavily substituted with Super A and Super T modified bases (commercially available from Epoch Biosciences, Inc., Bothell, Wash.) to achieve required stability for polymerase amplification. Longer oligonucleotides lead to increase secondary structures and primer dimer formation which reduced PCR efficiency. Probes and primers were designed with MGB Eclipse™ Software 2.0 that automatically assigns the substitution of A and T with Super A and Super T as required stability dictated. Probe sequence is shown in bold under lined and primer sequences are shown in bold only.

```
TTAACAAAAGTATTAGTAATCATATTACTTTTCTTAATCTGTGTGGTGAG

TACGTAAGTGTTCATTTCCATTCCATTAGTATTATATTTGAAAACTAAAA

ACTCCTGCGTAAGTCTCAATATAACTGCTTATGTCCATGTTCTATTTAAT

ACACCTTATAACCCATGTGTAGTGTGAACCAATAGCTGTGTTTTAATATT

TTTG[C/T]TAAATATATTATACATTCACTATAACCTC

TACAGTTTTAAAGAATGTTAAAATGAACCTGAATACCTAGTTT

CCTCTACCCACACCCTTCTCCCCCATACCAATCTTTACTTCACAATTCTG

TCAATTACAGCTTAGGAAGGTACT
```

Figure 8:
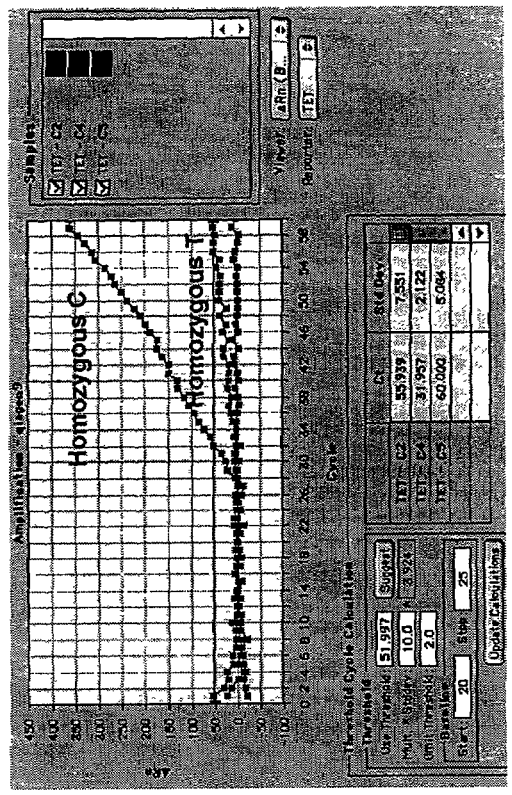
FIG. 8 illustrates the use of primers and probes with some normal bases substituted with modified bases to perform an assay in an AT-rich region.
Figure 8:
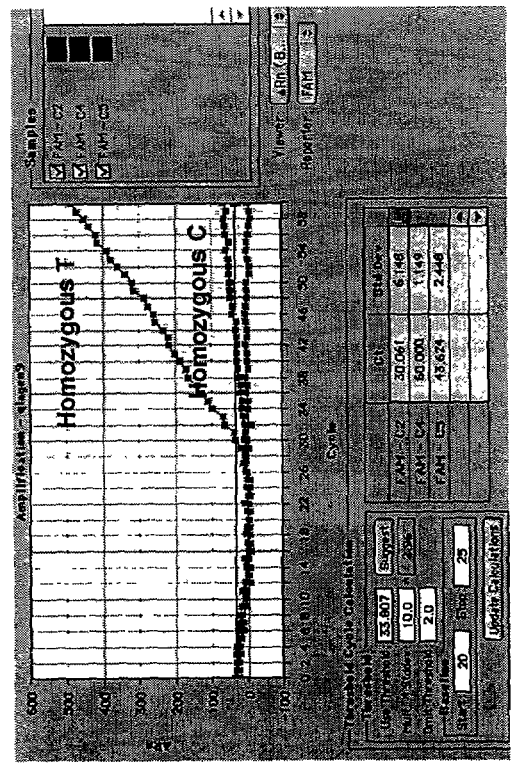

Probe and primer sequences are shown below where "a" is Super A and "t" is Super T. The use of modified bases allow the design of shorter probes and primers with improved mismatch discrimination as shown in FIG. 8.

```
Sense Primer 1: CCt GCG tAt GtC tCa ATA T
(SEQ ID NO:30)

Antisense Primer 2: CtG tAG aGG TTA TAG TG
(SEQ ID NO:31)

Probe "T" MGB-Q-TtG tTa AaT aTa TTa t-TET
MGB-Q-TtG tTa AaT aTa TTa t-TET
(SEQ ID NO:32)

Probe "C" MGB-Q-ttG CTa AaT aTa TTa T-FAM
(SEQ ID NO:33)
```

Example 7

This example illustrates the use of internal controls to monitor PCR inhibition.

In this exampel internal controls are used with a set of primers and a scrambled *C. elegans* sequence for the control.

All samples are spiked with a low amount of internal control template (about 10 to 10$^4$ copies) to screen for false PCR negatives. A whole internal control sequence was created without any significant homology with any known organism. Consequently, a different primer set is required from that of a gene of interest.

In one embodiment an internal control system is used that comprises a) a primers set that is different than the primers set used to amplify target, b) an internal control target that is longer than the sum of the internal control primers, and c) an internal control probe and wherein the sequences of the internal control primers and internal control probe are substantially different from that of known sequences.

---

Sequences of Internal Control Templates (IC) used in the tests

Universal IC (scrambled *C. elegans* sequence)
CTCAGGTGTCCGTGTGTTCCATCTGTTCTAGGCAAAGTCCCATCGTT
TCCACCAGTTACTTTACGGACCAC
(SEQ ID NO:34)

Forward Universal IC primer
CTCAGGTGTCCGTGTGTTCCAT
(SEQ ID NO:35)

Reverse Universal IC primer
GTGGTCCGTAAAGTAACTGGT
(SEQ ID NO:36)

Probe
MGB-Q-GGCAAAGTCCCATCGTT-Yakima Yellow dye
(SEQ ID NO: 37)

---

Figure 9:
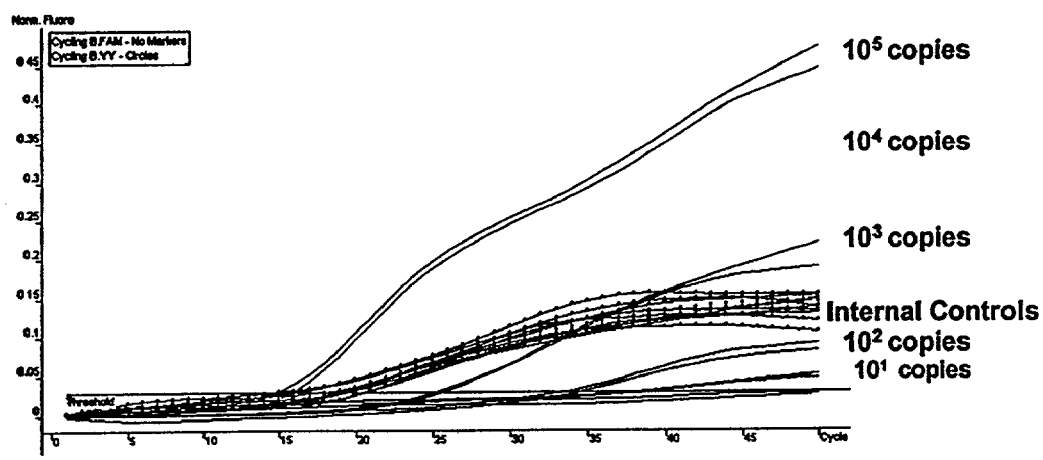
FIG. 9 illustrates a titration curve of a CapA target sequence (pOX2 plasmid, Bacillus anthracis genome), wherein each dilution contains a constant amount of the universal internal control with the appropriate primers sets.
Figure 10:
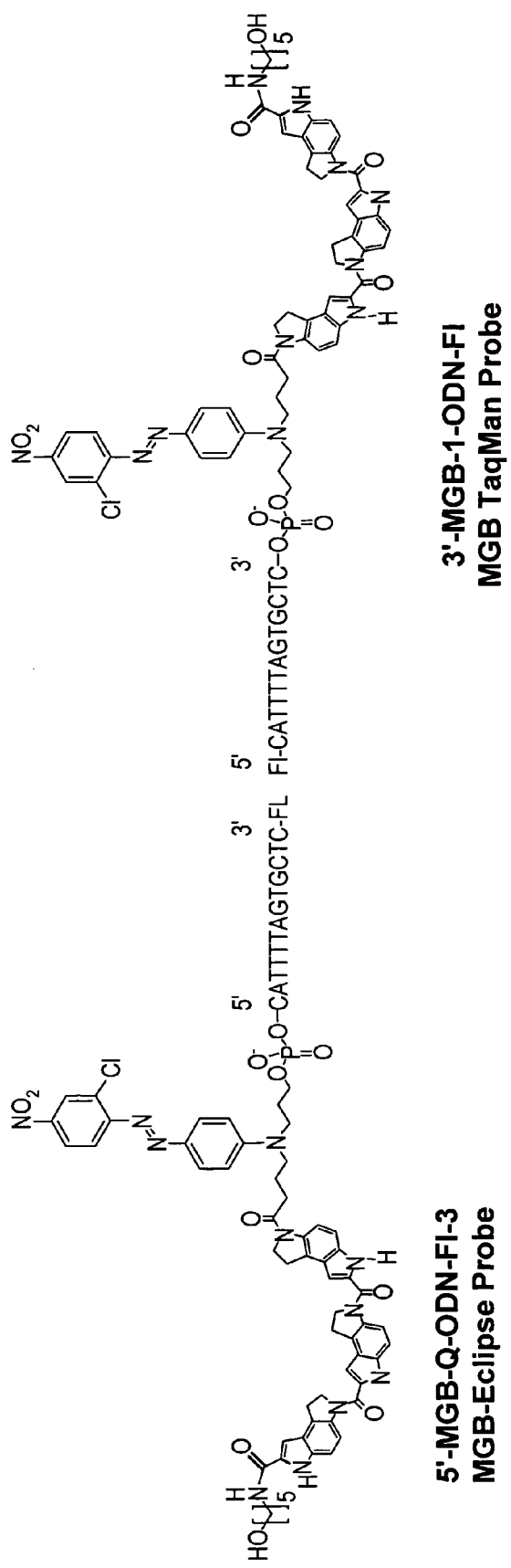
FIG. 10 provides structures of a preferred MGB-Eclipse™ probe (SEQ ID NO:6) and a related MGB Taq-Man® probe (SEQ ID NO:7). Fl represents a commercially available fluorophore as described in more detail herein, that can be attached using phosphoramidite coupling methods.

Internal control PCR is typically bi-plexed by using a fluorophore1-labeled specific probe and fluorophore2-labeled internal control probe mixed together. Fluorophore1 and fluorophore2 can be any suitable fluorescent dye. In practice it was determined that samples that contain PCR inhibitiors repeatedly did not amplify IC template and were qualified as "PCR inadequate". FIG. 9 demonstrates a titration curve of a CapA target sequence (pOX2 plasmid, *Bacillus anthracis* genome), each dilution contains a constant amount of the universal internal control with the appropriate primers s

TABLE 6-continued

Influence of Linker K on the Performance of Probes in a Real-Time PCR W=O—(CH$_2$)$_3$—N—(CH$_2$)$_2$—C(=O)—

| # | Sequence, 5' to 3' of Eclipse probe | K | Oligomer | % Fluorescence Increase |
|---|---|---|---|---|
| | CCG C-K-FL (SEQ ID NO:42) | | | |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for distinguishing between wild-type, mutant and heterozygous target polynucleotides, said method comprising:

(a) contacting a sample containing a target polynucleotide with two probes wherein a first probe is specific for said wild-type target polynucleotide and a second probe is specific for said mutant target polynucleotide, each of said probes having a formula:

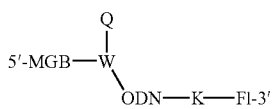

wherein MGB is a minor groove binder, Q is a quencher, W is a trivalent linking group, ODN is an oligonucleotide or modified oligonucleotide, K is a bond or a linking group and Fl is a fluorophore; wherein said first and second probes have different fluorophores and each of said probes forms a stable hybrid only with the target sequence that is perfectly complementary to the ODN portion of said probes; and (b) measuring the fluorescence produced on hybrid formation for each fluorophore, wherein said measuring is carried out at two wavelengths and is measured as a function of temperature, and using melting curve analysis to indicate the presence or absence of each of said wild-type, mutant and heterozygous target polynucleotides.

2. A method in accordance with claim 1, wherein the melting temperatures ($T_m$) for each hybrid produced between said first and second probes and their respective targets are within about 5° C. of each other.

3. A method in accordance with claim 1, wherein the ODN portion of each of said probes is an oligonucleotide or modified oligonucleotide having from 8 to 18 bases or modified bases.

4. A method in accordance with claim 1, wherein the ODN portion of each of said probes is an oligonucleotide or modified oligonucleotide having from 10 to 15 bases or modified bases.

5. A method in accordance with claim 1, wherein the fluorophore portions of each of said probes are selected from the group consisting of 5-FAM™, 6-FAM™, TET™, JOE™, HEX™, VIC™, NED™, TAMRA™, ROX™ and YY™.

6. A method in accordance with claim 1, wherein the ODN portion of each of said probes contains at least one modified base.

7. A method in accordance with claim 6, wherein each modified base is independently selected from the group consisting of 6-amino-1H-pyrazolo[3,4-d]pyrimidin-4(5H)-one, 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazol[3,4-d]pyrimidine-4-one, 6-amino-3-(3-hydroxyprop-1-ynyl)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine 2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-ynyl)-1,3-dihydropyrimidine-2-one, 6-amino-5-(3-aminoprop-1-ynyl)-1,3-dihydropyrimidine-2-one, 5-[4-amino-3-(3-methoxyprop-1ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazololl[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-d]pyrimidine-4,6-diamine, 3-chioro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chioro-1H-pyrazolo[3,4-d]pyrimidin-4-ylamine.

8. A method in accordance with claim 1, wherein said sample is further contacted with a set of primers under amplification conditions and each of said primers contains from one to ten modified bases selected from the group consisting of 6-amino-1H-pyrazolo[3,4-d]pyrimidin-4(5H)-one, 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-yny)1-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-ynyl)-1,3-dihydropyrimidine-2-one, 6-amino-5-(3-aminoprop-1-ynyl)-1,3-dihydropyrimidine-2-one, 5-[4-amino-3-(3-methoxyprop-1-ynyl)pyrazol[3,4-d]pyrimidinyl]-2-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol, 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione, 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chioro-1H-pyrazolo[3,4-d]pyrimidin-4-ylamine.

\* \* \* \* \*